US008828415B2

(12) United States Patent
Casaña Giner et al.

(10) Patent No.: US 8,828,415 B2
(45) Date of Patent: *Sep. 9, 2014

(54) MICROCAPSULES WITH ACETYLENE CARBAMIDE-POLYUREA POLYMERS AND FORMULATIONS THEREOF FOR CONTROLLED RELEASE

(76) Inventors: Victor Casaña Giner, Ebenfurth (AT); Miguel Gimeno Sierra, Ebenfurth (AT); Barbara Gimeno Sierra, Ebenfurth (AT)

( * ) Notice: Subject to any disclaimer, the term of this patent is extended or adjusted under 35 U.S.C. 154(b) by 0 days.

This patent is subject to a terminal disclaimer.

(21) Appl. No.: 13/489,208

(22) Filed: Jun. 5, 2012

(65) Prior Publication Data
US 2012/0245027 A1 Sep. 27, 2012

Related U.S. Application Data

(62) Division of application No. 12/225,890, filed as application No. PCT/EP2007/002810 on Mar. 28, 2007, now Pat. No. 8,216,598.

(30) Foreign Application Priority Data

Mar. 30, 2006 (EP) .................................... 06006748

(51) Int. Cl.
*A01N 25/28* (2006.01)
*A01N 43/00* (2006.01)
*A01N 53/02* (2006.01)
*A01N 57/02* (2006.01)
*A01N 65/00* (2009.01)
*B01J 13/16* (2006.01)
*C08G 18/38* (2006.01)
*A01N 43/80* (2006.01)
*C08G 18/76* (2006.01)

(52) U.S. Cl.
CPC ................ *B01J 13/16* (2013.01); *A01N 25/28* (2013.01); *C08G 2310/00* (2013.01); *C08G 18/3848* (2013.01); *A01N 43/80* (2013.01); *C08G 18/7607* (2013.01); *Y10S 514/963* (2013.01)
USPC ........... 424/419; 424/408; 424/409; 424/490; 424/764; 71/64.13; 427/213.34; 504/265; 504/280; 504/337; 504/355; 514/963

(58) Field of Classification Search
None
See application file for complete search history.

(56) References Cited

U.S. PATENT DOCUMENTS

| 4,056,610 | A | 11/1977 | Barber, Jr. et al. |
| 4,643,764 | A | 2/1987 | Scher |
| 4,837,403 | A * | 6/1989 | Aumueller et al. ........... 544/215 |
| 4,889,719 | A | 12/1989 | Ohtsubo et al. |
| 6,423,425 | B1 | 7/2002 | Faucher et al. |

FOREIGN PATENT DOCUMENTS

| WO | WO92/13448 | 8/1992 |
| WO | WO92/13450 | 8/1992 |
| WO | WO93/14865 | 8/1993 |

OTHER PUBLICATIONS

International Searching Authority, Written Opinion of the International Searching Authority issued in connection with International Patent Application No. PCT/EP2007/002810, mailed Sep. 30, 2008, 4 pages.
International Searching Authority, International Search Report issued in connection with International Patent Application No. PCT/EP2007/002810, mailed Aug. 2, 2007, 7 pages.

* cited by examiner

*Primary Examiner* — H. Sarah Park
(74) *Attorney, Agent, or Firm* — Vedder Price PC

(57) ABSTRACT

The present Invention deals with an alternative Interfacial polymerization process of microencapsulation, microcapsule's produced thereof, microencapsulated agrochemicals, pharmaceuticals, catalysts and phase transfer materials, and formulations thereof, by means of microcapsules and starting materials with the participation of acetylene carbamide derivatives in the final structure of the microcapsules' wall.

21 Claims, 12 Drawing Sheets

DEP

Fig. 7

GAT lambda-cyhalothrin 10 CS

Karate Zeon 10 CS

Particle Diameter (μm.)

Fig. 8. Release rate of capsules suspension formulations of lambda-cyhalothrin at 10 g/L.

Fig. 9. Release rate of capsules suspension formulations of lambda-cyhalothrin at 5 g/L.

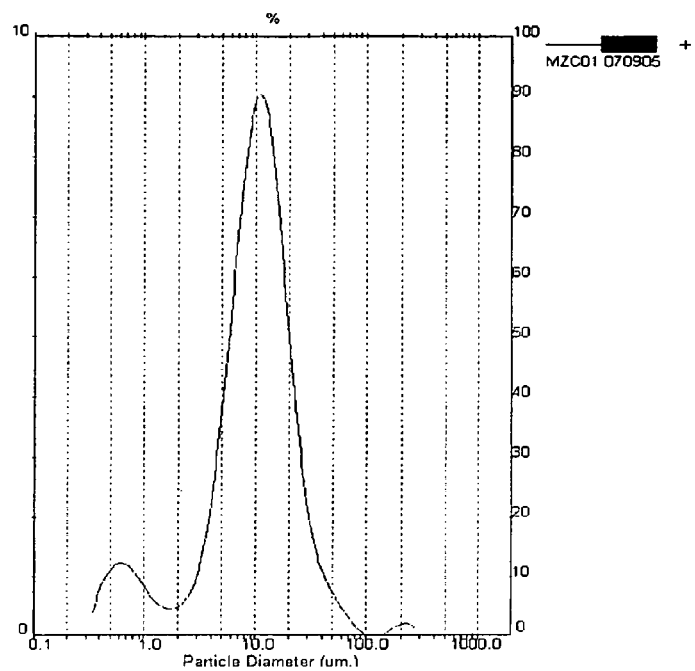
Fig.11. Particle size of Metazachlor 250.0 g/L + Clomazone 33.3 g/L ZC – Metazachlor 250.0 g/L + Clomazone 33.3 g/L ZC Fig. 12 Viscosity of Metazachlor 250.0 g/L + Clomazone 33.3 g/L ZC – Metazachlor 250.0 g/L + Clomazone 33.3 g/L ZC (MZC02 070905)
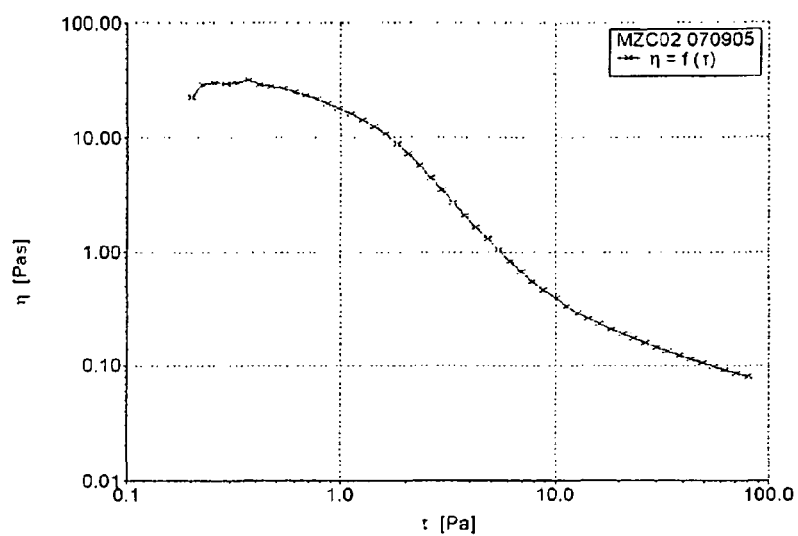

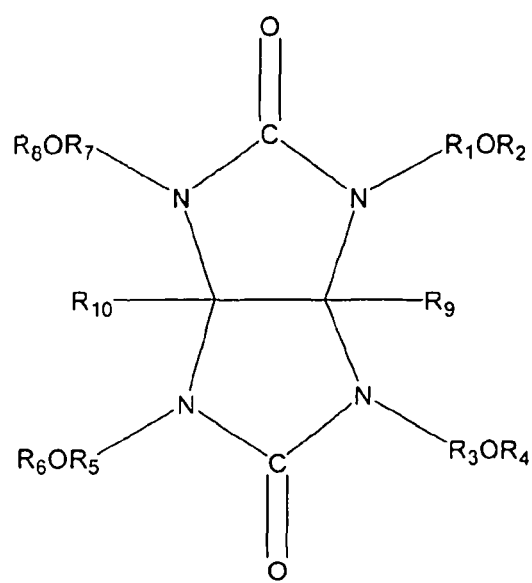
Fig. 13. Acetylene carbamide derivatives

MICROCAPSULES WITH ACETYLENE CARBAMIDE-POLYUREA POLYMERS AND FORMULATIONS THEREOF FOR CONTROLLED RELEASE

RELATED APPLICATION

This application is a divisional application that claims priority to and the benefit of co-pending U.S. patent application Ser. No. 12/225,890, entitled "MICROCAPSULES WITH ACETYLEEN CARBAMIDE-POLYUREA POLYMERS AND FORMULATIONS THEREOF FOR CONTROLLED RELEASE," which was filed on Sep. 30, 2008 which is a national stage entry of International Application No. PCT/EP2007/002810, which was filed on Mar. 28, 2007, the disclosures of which are incorporated herein by reference.

DESCRIPTION

The present invention deals with an alternative interfacial polymerization process of microencapsulation, microcapsules produced thereof, microencapsulated agrochemicals, pharmaceuticals, catalysts and phase transfer materials, and formulations thereof, by means of microcapsules and starting materials with much lower toxicological profile than customary microencapsulation materials, and with the participation of acetylene carbamide derivatives in the final structure of the microcapsules' wall.

FIELD OF THE INVENTION

This invention deals with polymer microencapsulation for controlled release of active ingredients and formulations containing microcapsules.

STATE OF THE ART

The problem addressed in the present invention is to provide a alternative microencapsulation process, and microcapsules thereof, for controlled delivery of agrochemicals (or other compounds with structures related with all the different types of agrochemicals' structures for any suitable process, also phase change materials—PCMs—, inks, thermosetting materials and catalysts) in such a way that the risks associated with the production and the product itself are decreased (by means of using wall forming materials with lower toxicity compared with present industrial processes) while the microcapsules produced thereof (and the formulated microcapsules) control the release rate in a suitable way for a proper functionality.

Microencapsulation methods for the delivery of agrochemicals are known since late 40's. Physical methods, phase separation and interfacial reaction are the three main procedures for microencapsulation. The most successful interfacial polymerization for microencapsulation of agrochemicals was developed on earlier 70's by Scher et al. (Stauffer Chemical Company), and many patents from Stauffer' group (later Zeneca, then ICI and nowadays Syngenta) have been granted based on modifications of the same initial concept, namely, the formation of a polyurea microcapsule's wall to enclose chemicals.

The present invention comprises several aspects. In this case, the field requires the synergistic or combined effects of many parameters, starting with the reactants, the materials to be encapsulated up to the final modifications for definitive industrially applicable formulations, especially in agriculture, for final proper functionality.

i) we disclose an industrial process of microencapsulation that has never been taught before, that includes the use of at least an aromatic isocyanate, and at least an aliphatic isocyanate and at least an acetylene carbamide derivative (ACDs) of formula (I) as wall forming materials.

ii) The enclosed materials in our microcapsule's have a particular release rate, in some embodiments being more beneficial than current commercial products, and in some embodiments being an alternative (less toxic) to current processes, ranging from fast release (e.g., lambda-cyhalothrin), maintained release, (e.g., fluorochloridone, clomazone) and practically no release, e.g. (phase change waxes).

iii) The agrochemical formulations described herein are novel and functionally acceptable, meaning that can be use in the field as current microencapsulated formulations are currently being used, with the same machinery, precautions and procedures that the farmer is used to, or the same use in fabrics and coatings for PCMs (phase change materials), or the same use in reactions for microencapsulated catalysts as the current microencapsulated catalysts.

iv) Dry formulations of the microcapsules can be used for microencapsulation of PCMs, by incorporating to the oil phase waxes or oils with melting points in the range of 0 to 50° C. (that may constitute the only oil solvent) or dispersing the solid materials in an appropriate oil phase, also for catalysts and thermosetting materials, Note that we will refer to Acetylene Carbamide Derivatives with the acronym ACDs.

We will refer to formulations of microcapsules in agriculture to any kind of agrochemical formulations that contain microcapsules, and not only to the common "Capsule Suspension" (CS) formulations. Non-limiting examples are that under our term "microcapsule's formulation" are suspoemulsions, as well as water dispersable granules containing microcapsules, oil suspensions where in the oil there are mixtures of agrochemicals (at least one microencapsulated), etc. Also, it is evident that our invention allows the combination of microcapsules enclosing one or more active ingredients with other non-microencapsulated active ingredients in the same formulation.

Our invention differs with regard the prior art in that:

There is an additional an essential cross-polymerization agent that gives unique characteristics to the microcapsules, namely, acetylene carbamide derivatives (ACDs).

The ACDs provoke drastic changes in capsule's wall permeability at low concentrations (starting at 0.05 to 5% of total formulation)

The polymer wall is not a polyurea wall (already claimed in many different patents), rather a polyurea-acetylene carbamide derivative wall (not disclosed ever before).

This wall presents an additional parameter—with respect to prior art—to control the permeability of the microcapsule's wall, namely, the ratio ACD/isocyanates, determined experimentally.

There is the need (not the option) to add a first catalyst for the formation of the polyurea bonds, because the microcapsules are restricted to the use of aliphatic isocyanates and aromatic isocyanates (that are less reactive) preferably dialkyltin fatty acid ester.

The avoidance of highly toxic isocyanates as those described in previous patents (as TDI) is allowed thanks to the novel combination of less toxic isocyanates able to form polyurea wall, ACDs' cross-linkers and catalysts adapted for our process, and the ability to terminate isocyanate functional groups unreacted.

The different materials to be encapsulated, reaction products, catalysts and chemistry involved, times and temperature reactions are in a whole unique features.

We are able to encapsulate with our process any chemical that is not intrinsically reactive with the functional groups of the wall materials, being this belonging to any structural chemical type, as long they do not react with the wall forming materials and the molecular size, ability to be dissolved, dispersed or used pure is suitable.

Customary and worldwide used microencapsulation materials for many agricultural formulations (sold worldwide in high amounts, e.g., Karate® Zeon—Syngenta—) use as a part of the wall the highly human-toxicant and carcinogenic compound 2,4-toluenediisocyanate (TDI), CAS# [584-84-9]. In our preferred embodiments we make use of isocyanates with highly reduced toxicological profiles than the mentioned TDI, for example m-TMXDI, CAS# [2778-42-9], sold as TMXDI® by Cytec. Worthy to note, TMXDI has not ever been reflected in a significant—if any at all—industrial use of it in the field of microencapsulation of liquids either agrochemicals, also not for other microencapsulations. As read in CYTEC webpage "TMXDI resins are commonly used in the tooling industry, and to encapsulate and protect electronics, coat printed circuit boards, and adhere seal filters". This render the combination of isocyanates with ACD absolutely novel and not obvious.

Below a comparison table of toxicological differences in between TMXDI and TDI (according MSDS of Sigma-Aldrich and CYTEC).

| TOXIC EFFECTS | TDI | TMXDI |
| --- | --- | --- |
| cancer | carcinogenic (Ames test) IARC carrcinogen 2B CMR Cat. Carcinogen 3 | not carcinogenic (Ames test) |
| acute inhalation toxicity ($LC_{50}$) | 10 ppm for 4 h - mice | 27 ppm for 4 h - mice |
| pulmonary sensitization in guinea pigs | Yes | no |
| affects respiratory system in humans at long term (3 y) | Yes | no |
| Flash point | >132° C. | >153° C. |
| Storage | | need to store under nitrogen only required to be stored at T < 8 |

Thus, apart form solving the problem to create microcapsules with allow a tailored release rate of chemicals, in this invention we improve the toxicological profile of the microcapsules (and formulations thereof). Important to mention, the prior art microencapsulation processes normally do not complete in full, then the rest of isocyanates unreacted are a health hazard for the end-users. Not only the use of ACD reduces the content of unreacted isocyanates. At the same time, any unreacted isocyanate present at the time of use of the microcapsules' formulation—either in the wall or dispersed/dissolved in the formulation itself—is of much lower toxicity (e.g., TMXDI vs. TDI).

U.S. Pat. No. 4,285,720 (originally filled in 1973 by Scher et al., Stauffer)—included here in full by reference—, shows the basic process of an interfacial microencapsulation. Other newer patents do not teach more than this document in regard our new invention. In U.S. Pat. No. 4,285,720 is claimed a process of microencapsulation with capsules of polyurea without addition of a second reactant, providing an organic phase—with a water immiscible material to be microencapsulated—and an organic polyisocyanate in an aqueous phase containing a solution of water a surfactant and a protective colloid and heating, whereupon said water-immiscible material is encapsulated within discrete polyurea capsular enclosures. No mention of ACDs is done. Moreover, a catalyst can be optionally added to speed up the reaction, said catalyst being alkyl tin acetate. In our invention a catalyst of the type of alkyl tin ester (preferably a dibutyl esther) is needed.

U.S. Pat. No. 4,874,832 describes microencapsulation process with aliphatic isocyanates, but combined with polyether polyols to form polyurethanes. U.S. Pat. No. 4,417,916 and U.S. Pat. No. 4,874,832 explain in detail microencapsulation with aliphatic isocyanates, but not combined with acetylene carbamide derivatives. U.S. Pat. No. 5,925,595 discloses the use of TMD and PAPI, and the influence of TMXDI in the release rate when the latter is included in the mixture of isocyanates. However U.S. Pat. No. 5,952,595 in a substantial way because the wall forming materials need the use of a polyamine (indicated in the description and also in the embodiments, where always an amine is used): in our invention we do need at all the use of a polyamine to form the polyurea wall, a tremendous difference with the present invention both regarding the chemical process and the final structure and characteristics of the microcapsule. Moreover U.S. Pat. No. 5,925,595 does not mention the use of ACDs.

One essential novel and inventive aspect of our invention is the use for the synthesis of the microcapsule's wall of ACDs. The existence of the own brochures of ACDs (e.g., Powderlink® 1174, from CYTEC) teach away from using them in a microencapsulation process, based on their low reactivity and the need of special initiators and temperature requirements, and the need of additional hydroxyl groups for their reaction.

In WO 92/13448 (equivalent of EP 571396 and U.S. Pat. No. 5,332,584) is stated that aminoplast polymers for its use in microencapsulation can be done with different types of compounds, namely: urea formaldehyde, melamine formaldehyde, benzoguanamine formaldehyde and acetylene carbamide (glycoluril-) formaldehyde. However in that document is not mentioned either implicitly suggested the use of any isocyanate compound to for part of the microcapsule's wall in combination with any urea, melamine, benzoguanamine glycoluril formaldehyde, as we do in this invention (independent claim 1 and dependent claim 4 of EP 571396 B1 deals with the only use of amino resin compounds, without isocyanates).

In the course of our research we found out that well away with respect to what was disclosed in prior art and in a extremely surpressively way, that we could introduce ACDs in a polyurea wall and at the same time, using a combination of isocyanates (in the preferred embodiment, PAPI and TMXDI) less toxic than the conventional mixture PAPI and TDI.

There are documents that teach away from the solution we have invented. Further prior art can be exemplarized by U.S. Pat. No. 5,563,224. There it is disclosed the use of compounds (including ACDs) to anchor UV protectants for the production of plastics, needing the ACD (to be reactive to anchor these UV protectors) the use of sulphuric acid. In the same patent, it is clearly stated that the acetylene carbamide monomers, in order to be reactive must be in strong acid conditions and under heat. Probably, in our process, the needed chemical potential needed for the activation of the ACDs is provided by the self isocyanate excited state and/or the localized increase of temperature of the exotermic isocyanate reaction. Must be quoted that U.S. Pat. No. 5,563,224 does not refer in any instance to polymers for its use in the particular and very specific field of microencapsulation. In our invention we do not use strong acids either strong heating (that could destroy the active ingredients to encapsulate).

The following documents have been cited in the Extended European Search Report, and are discussed regarding the novelty and inventive step in front of our invention. DD 108760 (Makower et al., 1974) discloses ACDs that in a very restrictive way (ethoxylates) could represent some of our compounds (I) and moreover for fields well distant from microencapsulation, like big pieces of plastic materials. No mention of combination to form polyurea microcapsules is made. WO 92/13450 (ICI, 1992) discloses in claim 1 only-polyurea compounds that are formed by the process of reacting isocyanates to form polyurea walls without addition of a second reactant, thus teaching away from the inclusion of ACDs. U.S. Pat. No. 4,889,719 (Ohtsubo et al., 1989) discloses a microencapsulated insecticidal composition comprising an organophosphorous insecticide encapsulated in a wall formed of a polyurea; however no hint as to form a combined polymer with ACDs is present. Further, U.S. Pat. No. 4,889,719 teaches away from the combination of an aromatic isocyanate and an aliphatic isocyanate as we do (col. 1, ln. 38-40: blends of aromatic and aliphatic isocyanates are not preferred, because the reaction rate difference between them does not readily produce a homogeneous wall). The inventors have found that this is not at all the case according our invention, since we get a very homogeneous wall, and, moreover, a very homogeneous particle size of the microcapsules. U.S. Pat. No. 4,458,036 (Fesman et al. 1984) deals with polyurethanes with ACDs incorporated, in a distant field as flame retardants, in form of foams, and not in microscopic structures as microcapsules. In between the thousands of reactions possible to be performed to form plastics or foams (in U.S. Pat. No. 4,458,036, mattresses, upholstery, cushion) that document does not provide any indication that the ACDs could be combined with polyureas to form microcapsules. The macroscopic structure of the polymers disclosed in U.S. Pat. No. 4,458,036 do not lead to homogeneous spheres of polyurea-ACDs polymers, either is envisaged any application of the cited polymers in the field of microencapsulation. U.S. Pat. No. 3,766,204 (Mathew C, U S et al., 1973) also deals with remote fields like polyesthers, alkyd resins and polyurethanes, lubricants and surface active agents. Moreover, the ACDs disclosed therein are absolutely different from those claimed in our invention. There is no hint why the ethoxylated chain should be disregarded from compounds disclosed in U.S. Pat. No. 3,766,204 to arrive to the claimed ACDs, and much lesser to choose them as participants in a polyurea-ACD wall for microcapsules. It is noteworthy that in a field of increasing interest as microencapsulation, the ACDs have never been disclosed to be used (not even as a mere possibility) in microcapsules.

Worthy to note is that the heating needed for microencapsulation processes (including ours) may be sometimes higher than the maximum limit of the stability of the chemical to encapsulate. This happens for example, in the particular of pyrethroids, where some undesired enantiomeric or diasteroisomeric or isomeric forms are increased due to the temperature. For those cases we have realized that the addition of antioxidants may prevent this isomerization. First of all, it is not obvious that an antioxidant may prevent isomerization (there are many chemical pathways in which a molecule might be isomerized) and second, the idea of incorporating antioxidants in an oil phase has never been disclosed for the case of isomerization of pyrethroids. By virtue of our process, we are able to add oil soluble antioxidants (for example, BHT—butylhydroxytoluene—, BHA—butylhydroxyanisol—or mixtures thereof) directly to our oil phase. In a particular example, a 0.05% of BHT and 0.01% of BHA (with respect the total weight percent of the whole oil phase) may be added to Solvesso 200 that at the same time is the solvent in a preferred embodiment of microencapsulation of supercyhalothrin (quantities of BHT, BHA or other antioxidants shall be used according the recommendations of the respective producers). This prevents isomerization of supercyhalothrin that start to occur already at 40° C. at dark.

The idea of adding an additional cross-linking material of low reactivity as ACDs (when compared that reactivity with prior art microcapsule's wall constituents, e.g., only isocyanates or aminoplast resins) to the polyurea wall is not obvious. Neither is expected that small percentages of ACDs can modify the release rate characteristics of the microcapsules in between the ranges needed for agricultural uses, either being useful to microencapsulate catalysts, thermosetting materials or PCMs (the latter cases needing a higher content of wall forming materials until the release rate is suitable for each desired purpose). Moreover, the fact that some ADCs (e.g., Powderlink 1174) are solid, would be disregarded at first chance, because is more convenient (and the prior art shows it) to use liquid materials as wall forming materials in the interfacial microencapsulation (incorporated in the oil phase). It is possible to incorporate solid ACDs in a dispersed form in the oil phase (e.g, by Atlox® LP-1 or LP-5 or LP-6) but we have seen that sometimes this lead to an excessive amount of unreacted ACD.

Even wanting to add a cross-linking agent to a polyurea wall to modify prior art walls, an expert would have chosen any cross-linking agent more reactive than ACDs. A few scientific papers have been written about chemistry and properties of ACDs as cross-linkers, but never referred to a microencapsulation method, rather in fields enough distant to be considered in a microencapsulation process (e.g., fabric processing, coatings for car paints, etc). The reader must not confuse the scarcely described properties of ACDs with their specific novel and inventive application in microencapsulation and must understand the complexity involved in a cross-linking reaction in the interphase of an oil and water phase, in situ, of two types of isocyanates and ACDs—far to be comparable with a plastic film forming or lacquers reaction. Even in described polymerization processes in those far technical fields with the intervention of ACDs, the remaining non-polymerized monomers must be stripped off or removed from the final product, circumstance that does not occur in our invention. In particular, polymers having pores of relative big size (but not microcapsules as closed volumes) can be formed with acetylene carbamide-formaldehydes, but constantly these processes show that the acetylene carbamide formaldehyde must be initially emulsified in a water phase. The chemistry behind those processes is well different to that of our invention.

BRIEF DESCRIPTION OF THE DRAWINGS

FIG. 7 shows the particle size distribution of a commercial formulation where the 20 microcapsules' wall is done only with isocyanates and a formulation according the invention.

FIGS. 8 and 9 show the release pattern of the formulations corresponding to the particles sizes shown in FIG. 7.

FIG. 11 shows the particle size distribution of a formulation according Example 9.

FIG. 12 shows the viscosity diagram of the formulation according Example 9.

FIG. 13 shows a general representation of compounds acetylene carbamide derivatives (ACDs).

DETAILED DESCRIPTION OF THE INVENTION

Figure 1:
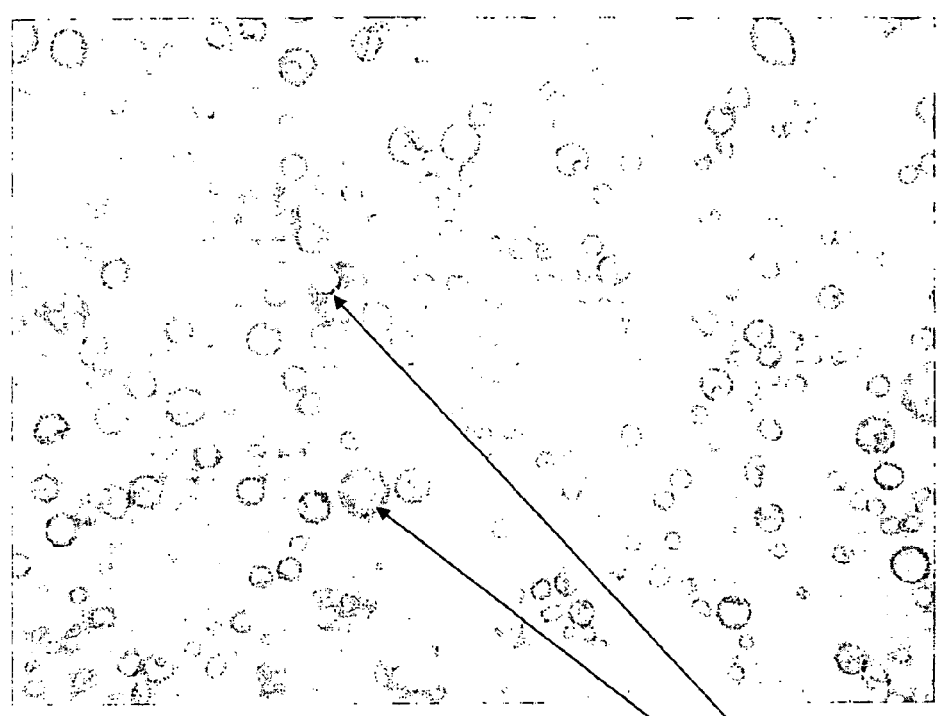
FIGS. 1 and 2 show the typical aspect under the microscope of microcapsules according the present invention, with the area "DEP" referring to an invagination or depression on the surface of the sphere-like structure.

The microencapsulation of active ingredient(s) in solution (organic phase) is done using interfacial polymerization processes based on the reaction of isocyanates with an acetylene carbamide derivatives of the formula (I).

Since the polymer that constitutes our microcapsule's wall is novel, particularly in the field of microencapsulation, we direct a set of claims to the polymer itself.

In particular, the polymer referred may be described as a polymer for microencapsulation of water-immiscible material, as a "primary" material to microencapsulate (or a mixture of water-immiscible materials). A "secondary" material to microencapsulate might be solid material dispersed in the oil phase to be microencapsulated together with the water-immiscible material and/or coformulants for technological reasons (surfactant) or protective reasons (e.g., antioxidants). It is obvious that the materials to be microencapsulated must be compatible and do not react undesirably before final use of the microcapsules. The "primary" material to microencapsulate is water-immiscible, meaning this in this case with a solubility in water lower than 750 mg/L at 20° C. Said claimed polymer is formed by means of an interfacial polymerization reaction and enclosing the water-immiscible material(s), characterized in that:

such polymer is formed by the reaction of:
   a monomeric aliphatic isocyanate
   a prepolymer aromatic isocyanate
   a N',N'',N''',N'''' alkoxy-alkyl and/or hydroxy-alkyl acetylene carbamide derivative or mixtures of such compounds where alkoxy means: methoxy, ethoxy, propoxy, isopropoxy, butoxy, isobutoxy, ter-butoxy, and alkyl means methy, ethyl, n-propyl, isopropyl, n-butyl, isobutyl, tert-butyl, sec-butyl, independently from each other substituted nitrogen
   and
   the microcapsules have a mean diameter of 0.3 to 25 μm, preferably in between 0.8 to 15 and 90% of the microcapsules have a diameter lower than 100 μm, preferably lower than 30 μm, when measured with a conventional laser diffraction particle sizer analyzer, previous customary dilution upon water under agitation The more hydroxyl groups present in the ACD, the more the reactivity. We have realized that an excessive number of hydroxyl groups per molecule of substituted ACD results in a faster reaction—appropriate in some cases—but more difficult to be controlled. The only way to select the right ACD for a particular purpose is to check experimentally the outcome of the reaction and adapt the reaction time (for example, by increasing/diminishing the speed in which the emulsification of oil droplets is taking place and/or increasing diminishing the quantity of the catalyst responsible for the formation polyurea bonds and the catalyst for the incorporation of the cross-linking ACD). It is possible that the alkoxy or alkyl groups are higher than a chain of 4 carbon atoms. In such case the capsule's wall is more permeable, due to the higher size of the cross-linking agent. The use of compounds up to 6 carbon atoms for the alkoxy and alkyl groups then needs to be reduced in the mixture of wall forming materials in order to avoid an excessive fast release. Also, more hydroxyl groups in the ACD causes an increase of reactivity, that may be appropriate for certain applications where a more tight wall structure is desired, for example in the case of phase change materials (PMCs). Our invention is directed to all kinds of ACDs, in between the range of substituents proposed, with regard of the stereochemical configuration. Normally, the use of these compounds is limited to what is commercially available, but a possible purification of a certain stereochemical structure in a future ACD won't deprive the use of such compound to be used as in our invention. A more defined structure of such polymer-participating a ACD (I) is as follows (FIG. 13):

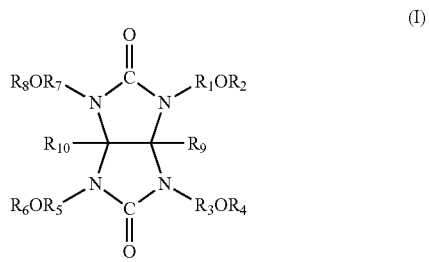

(I)

wherein
a) $R_1$, $R_3$, $R_5$, $R_7$, are, independently one to each other, methylen, ethylen, n-propylen, isopropylen, n-butylen, isobutylen, sec-butylen, tert-butylen
and
b) $R_2$, $R_4$, $R_6$, $R_8$, are, independently one to each other, hydrogen methyl, ethyl, n-propyl, isopropyl, n-butyl, isobutyl, sec-butyl, tert-butyl
and
c) $R_9$, $R_{10}$ being hydrogen or hydroxymethyl, more preferably both substituents being hydrogen, comprising compounds (I) all isomeric and stereoisomeric configurations that may be present depending on the radicals as cited, and been excluded from compounds (I) all the combinations of radicals that are not able to form polyurea-acetylene carbamide derivative (ACD) polymers when such ACDs are reacted as described in the present invention with a mixture of isocyanates.

The ACDs are a fundamental part of the wall of the final microcapsules in our invention. In a typical process we have two phases, an oil phase and a water phase, the oil phase is emulsified into the water phase at 45-70° C., the polyurea reactions start to take place, temperature is raised to 60-90° C., and the catalyst to make reactive the ACDs is placed—after the polyurea reactions start to take place—in the continuous water phase. A curing time of about 1 to 4 hours is set at 50-90° C. Then a unique polymer constituting the microcapsules' wall is formed in the water-oil interphase of the oil droplets.

A typical oil phase according to our invention is composed of:
   Monomer aliphatic isocyanate (e.g., TMXDI)
   Prepolymer aromatic isocyanate (e.g., PAPI)

Monomer acetylene carbamide (e.g. tetra-butoxymethyl acetylene carbamide) (referring to "monomer acetylene carbamide" when the content in monomers is higher than 50% of the total commercial acetylene carbamide product: in industrial conditions is difficult to have a pure monomer acetylene carbamide product)

Solvent (e.g., cyclohexanone to dissolve tetra-butoxymethyl acetylene carbamide)

Active ingredient(s) (e.g., supercyhalothrin)

Optionally, dispersed solid active ingredients (e.g., milled alpha cypermethrin at crystal sizes of <5 μm and Atlox® LP-1)

Optionally, dispersed and/or dissolved antioxidants and/or UV protectors

Optionally (for achieving smaller microcapsules' sizes) a surfactant with low HLB (e.g. Atlox® 4912)

The ratio of the composition is typically the following:

Monomer aliphatic isocyanate: Prepolymer aromatic isocyanate from 1:3 to 1:1

Prepolymer aromatic isocyanates: Monomer acetylene carbamide from 9:1 to 4:1

Monomer aliphatic isocyanates to: Monomer acetylene carbamide from 2:1 to 5:1, being the most preferred ration Monomer aliphatic isocyanate: Prepolymer aromatic isocyanates:

Monomer acetylene carbamide of 3:6:1.

Always, the oil phase is kept until emulsification in dehydrated atmosphere (by chemical or physical means, like desiccation or adsorption or isolation, and also possible to working under inert atmosphere, with gases preferably $CO_2$, $N_2$, He, or just controlling the relative humidity of the reaction site).

The water phase typically contains:

Water

Primary surfactant (e.g., an alkyl ethoxylated/propoxylated copolymer of type Symperonic®)

Water soluble or dispersable polymer(s) (e.g., polivinilpyrrolidone PVP-30)

Hydrocolloid(s) (e.g., Guar gum)

Lignosulfonate(s) (e.g., type of Kraftsperse®)

At this stage, during the dispersion process, the organic phase is emulsified into the aqueous phase at a temperature of about 45-70° C. The main particle size of the dispersed phase should be in the range of 1-25 μm. Once the target particle size is reached the high shear agitator is stopped and the main agitator (anchor) is adjusted to its lowest setting to reduce shear stress during heating up as curing period.

The catalyst present in the organic phase initiates the wall forming reaction that will be furthermore increased by heating up to about 60-90° C. Then is added the catalyst for the ACD incorporation to the polyurea wall, (e.g. p-Toluenesulfonic acid dissolved in an alcohol with a chain with no longer than 8 carbon atoms; if a substituted sulfonimide is used, then, the reaction temperature must be higher). The microcapsules are left from one to about two hours at 50-90° C. to complete termination of isocyanate residues. Then the mixture is allowed to cool down, normally, to room temperature.

The pH value of the cured microcapsule suspension is adjusted to the pH more appropriate for the stability and desired properties of the agrochemical, with a 50% aqueous solution of sodium hydroxide.

Finally, viscosity modifiers of the type of clays (e.g., inert zeolites) and hydrocolloids (e.g., xanthan gum), aluminum sulfate and sodium tripolyphosphate are added to prevent the microcapsules from separating from the water on prolonged storage due to their density difference. As a buffer system (preferably for economy reasons based on sodium carbonate or in citric acid) is applied to maintain the formulation at the desired pH. It is also interesting, for solutions to be at alkaline conditions, to use sodium carbonate (or any other source of carbonate ions) because adsorbs carbon dioxide generated from the reaction of residual isocyanates with water on storage therefore preventing any pressure buildup in the final product containers, situation only expected on exceptional cases when a batch has not been correctly terminated.

Any biocide is added to protect the formulation from biological attack during the shelf life of the product (preferably of the type of imidazolidinyl urea or other conventional bacteriostatics, bactericides or microbicides).

The process, as explained, starts by dissolving aliphatic and aromatic isocyanates and the active ingredient-eventually a surfactant, or UV protector or antioxidant—in a water-immiscible solvent. The solvent is present to dissolve the active ingredient(s)—a.i.—, in the case that the a.i. is a solid, or just to provide an oil phase where the a.i. is present. In certain cases, if the amount of a.i. is high enough, and is able to dissolve all the wall forming materials, the "solvent" is materially replaced by the a.i. itself, that acts both as a.i. and a solvent (being this situation exceptional). The ACD is incorporated into the oil phase with the aid of a second solvent, when needed. Further the oil phase contains the catalyst that will initiate the wall forming reactions (when in the presence of water). Also, solid active ingredients might be dispersed in the oil phase. The aqueous phase serves as the carrier medium (continuous phase) for the microcapsules that containing active ingredient(s), but the water phase may also contain dispersed or dissolved active ingredients (e.g., glyphosate or diquat for agricultural applications). The water phase is prepared by addition of emulsifiers, protective colloids and other coformulants that have the function of emulsify the oil droplets that will be the core of the final microcapsules and optionally, also serve as final coformulants needed for the proper functionality of the finished formulation.

Preferred Wall Forming Materials

Regarding ACDs we prefer the use of Powderlink® 1174 and Cymel® type commercial products, more preferably Cymel® 1711 and Cymel® 1170. The use of prepolymers of Cymel type result in a more irregular reaction course when compared with the use of Powderlink® 1174 in the specific trials we have done. Therefore the most preferred ACD is Powderlink® 1174. Must be noted that the commercial products might have some other compounds than the monomers referred in the label (e.g., Powderlink® 1174 may contain oligomers)

For the polyfunctional isocyanate system, we prefer one aliphatic isocyanate and one aromatic isocyanate (aliphatic refers to the fact that the —NCO group is not attached directly to the aromatic ring). The polymer density can be varied by changing the ratio of polyfunctional (e.g. prepolymer aliphatic PAPI) to polyfunctional aliphatic isocyanate (e.g. Cythane® 3174, TMXDI, the latter the preferred aliphatic isocyanate according this invention). The higher the ratio, the more cross-linking and hence the lower the diffusion coefficient and hence the lower the permeability. When incorporating the ACD, the complexity of the cross-linking reactions makes difficult to predict the final release rate, that can be measured by experimental trials with the formed microcapsules.

The preferred aromatic isocyanate according to our invention is PAPI® and its series from Dow®. Below is depicted a type of preferred compounds:

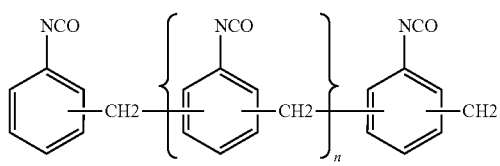

Wherein n=0 to n=6

For n=1, PAPI, CAS# [009016-87-9], commercial name Specflex® NE 138.

The preferred aliphatic isocyanates are TMXDI and Cythane® 3174, represented by the formulas below:

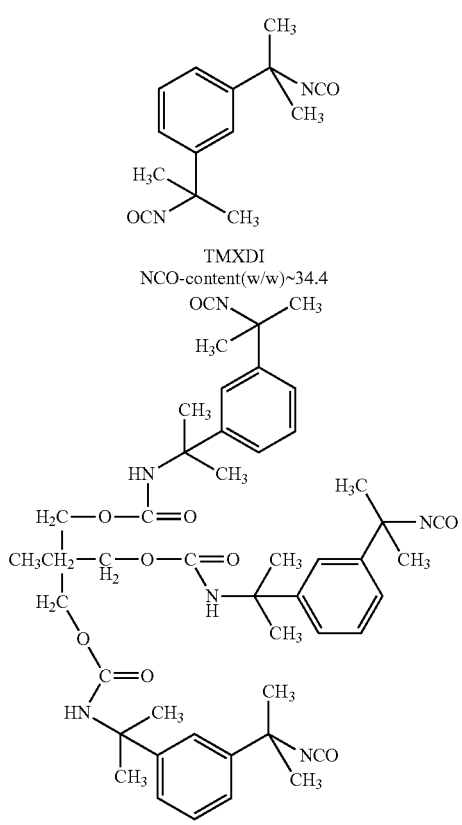

Cythane 3174-Pre-polymer in Butyl Acetate
NCO-content(w/w)~10.2

It is obvious that the benefit of incorporating acetylene carbamide derivatives into a wall formed of TDI and PAPI is possible, however, in that case, the production process and the capsules themselves have the problem of the intrinsic toxicity of TDI, in other words, the use of acetylene carbamide derivatives and TDI and PAPI is an obvious extension of the subject matter of this invention, as well as any customary combination of isocyanates to form polyurea walls. We have the experience that ACD can be incorporated into many types of polyurea walls, resulting polyurea-ACD polymers.

Also, the inventors have realized that inclusion of other aromatic isocyanates other than corresponding to the formula above leads to fully functional microcapsules' walls.

The use of aliphatic isocyanates (NCO groups are not directly bounded into the aromatic ring) implies the use of a catalyst to start the reaction due to their low reactivity. Due to this implicit lack of reactivity they are not used in industrial applications of commercially successful microencapsulated formulations.

We use catalysts (for the oil phase) like Stannous octoate, Dibutyltin dilaurate, Potassium acetate, Potassium octoate, Dibutyltin mercaptide, Dibutyltin thiocarboxylates, Phenylmercuric propionate, Lead octoate, Alkaline metal salts, ($K_2CO_3$, $NaHCO_3$ and $Na_2CO_3$), Ferric acetylacetonate.

We have been using the combination of tertiary amine catalysts for long time but we have surprisingly found that with the use of ACDs, and in the absence of amines, the reaction not only takes place, but in a manner highly convenient. According to our experience, a more particularly of the type mono-(di-, tri-, tetra-) fatty acid ester of alkyl element of the group 4 or group 14 fatty acid ester, being preferred as alkyl groups: methyl, ethyl, n-propyl, n-butyl, n-pentyl, n-hexyl, n-heptyl, n-octyl (and all their chain-isomeric forms), being the preferred metals transition metals Sn, Ti, In, Sb, Pb, Ge, Pd, Pt, Au, Zn, Fe, Cu. The most preferred catalyst for the type of microencapsulations asked currently in the agrochemical market is, by the cost, specific process needs and ecotoxicological reasons, the dibutlytinlaurate. We have compared the use of triethylendiamine with dibutyltinlaurate with only the dibutyltinlaurate catalyst and we have a higher improved control of the reaction and modification of wall properties when using only the dibutyltinlaurate. However, the process can be adapted (specially reaction time and temperature) for other suitable catalysts mentioned above for particular uses, especially agrochemicals with certain tendency to react with the wall forming materials.

For the incorporation of the ACDs to the wall, is used a second catalyst placed in the water phase, most preferably p-toluensulfonic acid or of the sulfonimide type (e.g. methyltolylsulfonimide) or of the type Cycat™600 or Cycat™500.

Our preferred polymerization system is using aliphatic isocyanates (m-TMXDI as monomer) in combination with the aromatic isocyanate PAPI that are less reactive than applying two aromatic isocyanates as e.g. PAPI/TDI. Additionally, the aliphatic isocyanates are produced without phosgene and free of nitrosamines. These types of isocyanates are advantageous in the toxicogical profile that makes it easier to work more safely than with other isocyanates have been established, for example the microcapsule's type of products of Syngenta, being this selection of type of isocyanate pair in a real industrial application completely new (in a higher degree of novelty, the combination with ACDs and the selection of only one organometallic catalyst).

The most preferred functionality of the lignosulfonates (that may also be achieved by other equivalent commercial products that can replace Kraftsperse without being lignosulfonates, but not as a primary option) is achieved by our own treatment of a mixture of the compounds below cited, by thermal treatment at 70° C. for 10 min, called LignoGAT™.

| Ingredients of LignoGAT ™ | wt % |
|---|---|
| Water | 72.2 |
| Celvol ™ 205 | 10 |
| Kraftsperse ™ 25M | 17.8 |
| Total | 100 |

Other lignosulphonates and modified sulfonates of choice are Reax®, Polyfon®, Kraftsperse®, Borresperse®, Ultrazine®, Ufoxane®, Marasperse®, Diwatex®, Morwet® in any of their variations.

Other suitable hydrocolloids are agar, alginates, carrageens, gellan gum, pectins, cellulose, exudated gums (arabic gum, tragacanth, *Ceratonia siliqua* gum and/or karaya gum), tragacants, saponines, xanthan gum, and derivatives and or mixtures of the named compounds.

Water soluble pr dispersable polymers of choice are, apart from the most preferred polyvinylpyrrolidone (up to 100 mols of monomer) and polyvinylacetate, copolymers of PVP and methylmethacrylate, copolymers of PVP and vinylacetate (VA), poylvinyl alcohol (PVA), copolymers of PVA and crotonic acid, copolymers of PVA and maleic anhydride, hydroxypropyl cellulose, hydroxypropyl guar gum, sodium polystyrene sulfonate, PVP/ethymethacrylate/methacrylic acid terpolymer, vinyl acetate/crotonic acid/vinyl neodecanoate copolymer, octylacrylamide/acrylates copolymer, monoethy ester of poly(methyl vinyl ether-maleic acid), and octylacrylamide/acrylate/butylaminoethyl methacrylate copolymers, acrylic acid/t-butyl acrylate copolymers, dimethylaminoethyl methacrylate/isobutyl methacrylate/2-ethylhexyl-methacrylate terpolymers, t-butylacrylate/acrylic acid copolymers, and silicone grafted terpolymers, e.g. t-butylacrylate/acrylic acid/PDMS and mixtures thereof.

The surfactant to form the emulsion of oil in water can be chosen in between a wide range of customary surfactants with the condition that the hydrophilic-lipophilic balance is in between 12 to 18 (e.g., ethoxylated and/or propoxylated alcohols).

Typical polyisocyanates suitable for this process are chosen from the first group and from the second group (for a two-isocyanate mixture as wall forming material—except the acetylene carbamide—, one isocyanate of each group must be taken, always must be at least one isocyanate of each group, due to confusing terminology in this area we point out other classification different that our simple division in between "aromatic and aliphatic"):

GROUP 1 [named as "aromatic" in our invention]—with NCO groups directly bound to the (substituted) bencene ring—:
  1,3- and/or 1,4-phenylene diisocyanates, 2,4-, 2,6-tolylene diisocyanates (TDI), crude TDI, 2,4'-, 4,4'-diphenyl methane diisocyanate (MDI), crude MDI, 4,4'-diisocyanatebiphenyl, 3,3'-dimethyl-4-4'-diisocyanate biphenyl, 3,3'-dimethyl-4,4'diisocyanate diphenylmethane, naphthylene-1,5-diisocyanate, triphenylmethane-4,4', 4"-triisocyanate, m- and p-isocyanate phenylsulfonyl isocyanate, polyaryl polyisocyanate (PAPI), diphenylmethane-4,4'-diisocyanate (PMDI)
  and derivatives and prepolymers of the GROUP 1 isocyanates.

GROUP 2 [named all of them as "aliphatic" in our invention]—with NCO groups not directly bound to the (substituted) bencene-ring-.
  Aliphatic isocyanates: ethylene diisocyanate, hexamethylene diisocyanate (HDI), tetramethylene diisocyanate, dodecamethylene diisocyanate, 1,6,11-undecan triisocyanate, 2,2,4-trimethylhexa-methylene diisocyanate, lysine diisocyanate, 2,6-diisocyanate methyl caproate, bis(2-isocyanate ethyl)fumarate, bis(2-isocyanate ethyl) carbonate, 2-isocyanate ethyl-2,6-diisocyanate hexanoate, trimethylhexamethylene diisocyanate (TMDI), dimer acid diisocyanate (DDI).
  Alicyclic Polyisocyanates: isophorone diisocyanate (IPDI), dicyclohexyl diisocyanate, dicyclohexylmethane diisocyanate (H-MDI), cyclohexylene diisocyanate, hydrogenated tolylenediisocyanate (HTDI), bis (2-isocyanate ethyl)-4-cyclohexene-1,2-dicarboxylate, 2,5- and/or 2,6 norbornane diisocyanate
  Araliphatic Polyisocyanates Having 8 to 15 Carbon Atoms m- and/or p-xylylene diisocyanate (XDI), alpha-, alpha-, alpha-, alpha-tetramethyl xylylene diisocyanate (TMXDI)
  Alicyclic Polyisocyanates: ethylene diisocyanate, hexamethylene diisocyanate (HDI), tetramethylene diisocyanate, dodecamethylene diisocyanate, 1,6,11-undecan triisocyanate, 2,2,4-trimethylhexa methylene diisocyanate, lysine diisocyanate, 2,6-diisocyanate methyl caproate, bis(2-isocyanate ethyl)fumarate, bis(2-isocyanate ethyl)carbonate, 2-isocyanate ethyl-2,6-diisocyanate hexanoate, trimethylhexamethylene diisocyanate (TMDI), dimer acid diisocyanate (DDI)
  And derivatives and prepolymers of the GROUP 2 isocyanates Further components of a formulation according of our invention can be found in pages 222 to 230 of the book (the mentioned pages incorporated herein in full by reference) Peter A. Lovell and Mohamed S. El-Aasser, Emulsion Polymerization and emulsion polymers, John Wiley and Sons, ISBN 0-471-96746-7, 1997, West Sussex.

An skilled in the art is able to identify which combination of isocyanate of the group 1 and isocyanate of group 2 will be suitable a priory, and which reaction conditions (dialkyltin fatty ester catalyst, temperature, time) are needed to reproduce the invention. In a wide range of combinations, the ACDs will react without problems, except when both types of isocyanates are of very low reactivity and/or the sites for attaching the N-substituted acetylene carbamide moieties are not appropriate.

The release rate of the microcapsules is mainly controlled by:
  Microcapsule size
  Degree of cross-linking
  Choice of polymer type
  Wall thickness
  Mobility of the oil phase The average particle radius (hence surface area) is generally fixed within narrow limits to satisfy process and physical stability considerations. The preferred average particle size of the droplets of the water-immiscible liquid containing the active ingredient is 0.1-200 μm, preferably 0.3-50 μm and more preferably 0.5-20 μm depending on the target. The size of the particles can also be below 0.1 μm. These particles are called nanoparticles, and this can be achieved by an appropriate emulsifier (specially incorporating it to the oil phase) and with an increased speed rate of the shearing-stress while the emulsification takes place. It must be understood that the use of the polymeric material of this invention in nanocapsules is an obvious application of this invention.

Particle size can be adjusted according to the end use of the microcapsules by adjusting stirring speed and time, and by the choice of surfactants and the amount of surfactants employed.

The concentration difference across the wall is generally considered to be a constant when the microcapsule is exposed to a foliar, water or soil environment. The foliage or soil acts as a sink for the pesticide and hence pesticide exists at a very low concentration at the outer surface of the microcapsule. Of particular interest is the use of microcapsules in lakes or water deposits to release insecticides against mosquitoes (e.g., pyriproxyfen, methoprene, hexaflumuron), where the water is the referred "sink".

If the release rate from the microcapsule needs to be varied over orders of magnitude, the most practical way of accomplishing this task is to vary the microcapsule wall permeability. The permeability is defined as the product of the factor diffusion coefficient and the factor solubility coefficient. For a given pesticide the diffusion coefficient can be varied by varying the wall thickness and by varying the cross-link density of the wall; varying the chemical composition of the wall can vary the solubility coefficient. Moreover the chemical structure of the solvent used for the active ingredient has an influence on the permeability/mobility and in the release rate.

The amount of the organic polyisocyanate and ACD used in the process will determine the wall weight of the microcapsules formed. In general, the amount of wall forming material comprise usually from about 2 to about 75 percent by weight of the microcapsule. Most preferably the wall will comprise from about 4 to about 15% by weight, of the microcapsule.

In the case of our invention the amount of wall forming material is about 2-20% of the oil phase. For a preferred amount of 6% of wall material, the wall thickness for a microparticle with a mean diameter of 10 μm can be calculated and is in the range of 100 nm.

For applications where the microcapsules need a specially smaller size (e.g., from 0.5 μm to 10 μm of average particle size, most preferably from 1 μm to 5 μm, the inventors have found that a oil-soluble surfactant of the type Atlox® 4912 added to the oil phase before emulsification step, decreases significantly the particle size. Other block copolymers can be used, preferably composed of polyglycol (e.g., polypropylenglycol) and poly fatty acids hydroxylated. A preferred concentration in the oil phase is about 5 to 25% of the weight percent of the sum of wall forming materials.

It is impossible to describe in full in the limited space of a patent disclosure how any formulation could be achieved using our process. A skilled in the art would need some experimental work to carry out the invention. The disclosure of the description and the of the examples is in the line of the accepted granted patent documents, even more detailed in how to manage to obtain microcapsules in between the range of compounds claimed. With regard of formulations of microcapsules, note that this type of formulations (capsule suspension—CS— and suspoemulsions—SE—) are tremendously complex per se. Documents providing basic and advanced knowledge of formulation technology that will allow the skilled in the art to reproduce our invention with unduly burden are: The e-Pesticide Handbook, British Crop Protection Council; Asaji Kondo. Microcapsules. (1970) Nikkan Kogyo Shinbun Ltd.; and Kondo et al. Microcapsules (1977) Sankyo Publishing Co., Ltd; Asaji Kondo. Microcapsule processing and technology (1979) Marcel Dekker Inc.; N. Cardarelli. Controlled release pesticide formulations. CRC Press (1976).

It cannot be denied the complexity of the microencapsulation technology, complexity added in the field of formulation of microcapsules. Critical steps are the emulsification step, that may lead to a phase inversion if the equipment used (ultraturrax, anchor agitators, pumps) is not very well known to the user, is critical also, the management of low relative humidity, reaction times and temperatures adapted to the vessels where the examples are reproduced, etc. For instance, in Example 1 it has been used a reactor of 2000 L, the repetition of the same example in a laboratory reactor needs the application of chemical engineering knowledge to reproduce in the same way the reaction in a small reactor (e.g., 500 mL) the heat transfer conditions and the turbulence and shear stress produced in such 2000 L reactor.

Our invention is mainly devoted to agrochemical formulations, but by the virtue of the type of wall material (polyurea+acetylene carbamide), the microcapsules have a glass transition temperature within the range of room temperature to 200° C., so the material for a capsule wall of a microcapsule obtained shows a heat response and they are suited to form thermosensitive recording materials, and all applications derived thereof (inks, fabrics, etc.). For the use of our microcapsules in the field of phase change materials, the process is similar to that already described. In this case, it is preferred a final product with dried microcapsules, that is easily achieved by conventional spray-drying of our microcapsules. In this case, it is not important the presence of the specific emulsifiers or hydrocolloids in order to get a wet formulation of microcapsules for its later use to dilute in water (as is the case in most agrochemical formulations). In the case of application of our invention to phase change materials, the main difference is in that the oil phase is mainly composed of a wax or oil—e.g. hydrogenated vegetable oil—that is able to store and release heat (normally with a melting point in between 0 to 50° C.), together with the wall forming materials, the catalyst (preferably dibutyltinlaurate) and eventually and additional solvent of high boiling point and low vapour pressure, to facilitate the microencapsulation of the wax.

It is important to note, that in order to adapt our microcapsules to these applications (e.g., dry microcapsules for boots, gloves, foams for seats, overall equipment, clothes) the release of the active ingredient (e.g. a wax of melting point of 37° C.) must be avoided correspondingly. The water phase, as explained in the description above, is then only the carrier medium that contains the necessary dispersants, protective colloids, etc. that are needed for obtaining a suitable dry formulation of microcapsules (and not a water phase that contains coformulants for final agricultural applications, rather coformulants directed for spray-drying or other means to remove water and obtain fluid compositions of microcapsules). Of course agricultural formulations containing our microcapsules in a dry state are very suitable with our microcapsules, but then, the water phase must be provided with the state in the art dispersants, wetting agents, etc., to be functional in the field, thing not needed when microencapsulating catalysts or PCMs.

We won't extend in this aspect, because the technique of obtaining dry microcapsules is well-known for the expert in the field, and our invention does not involve any novelty in this regard. However, our invention provides the novelty of a new type of microcapsules containing such PCMs (or thermosensitive recording materials, or catalysts). For this application, then the wall forming materials must be present about 5 to 10 times more (keeping the same ratios) in order to restrict the release of the compounds, and to extend the life of the microcapsules. This is indeed a controlled release rate, but with the target of the slowest release rate possible. The "four-fingered" cross-linking provided by our invention of incorporation of the ACDs, (one "finger" for each substituted nitrogen) allows more flexibility to the microcapsules to resist the pressure stress in such applications with PCMs (that in turn is also beneficial in agricultural applications with respect stress during production, packaging of formulations and final use by the farmer in the field—e.g. pressure in the spray nozzles—).

In the case of microencapsulation of catalysts, it is obvious that a dispersed catalyst in the oil phase (for example by using Atlox® LP-5 or other oil dispersants) possible to be used as core liquid dispersion to encapsulate. Already state in the art catalysts (e.g., platinum or palladium catalysts or osmium tetroxyde) are obvious applications of our invention, namely, to use the advantages or differences of our wall made of ACD-polyurea compared with common polyurea microencapsulation of catalysts. All the differences mentioned in this document with regard ACD-polyurea vs. polyurea walls can be applied for such catalysts.

The examples are thus directed to the more complex field of agrochemical formulations provided are a clear proof that given a target agrochemical formulation, regarding chemical and physicochemical characteristics, our invention leads (thanks to the uniqueness of the acetylene carbamide monomer characteristics and process characteristics) to accomplish the task, because we can chose appropriate quantities of isocyanates (here is disclosed for the first time the real use and good functionality of reactions using less toxic and reactive isocyanates like TMXDI) and the further parameter new in this invention, the acetylene carbamide monomer, for matching any demand in terms of particle size, release rate; being the rest of the coformulants chosen to match the desired density and viscosity and rest of chemical and physicochemical characteristics, chosen by routinary error and trial tests or by conventional microencapsulation technology techniques and methods.

For the purpose of this invention, if the skilled in the art wants to reproduce it, it is almost irrelevant which material is wanted to be microencapsulated. In the case of agrochemicals, the only restrictive condition is that they do not react with the wall forming materials, thing that can be evaluated by a chemist by the sole view of the corresponding functional groups of the wall forming materials and the agrochemicals. With respect of which combinations are adequate, the skilled must be referred to a general book of incompatibility of agrochemicals, or the own brochures of the agrochemicals' manufacturers. Techniques of milling and dispersing materials in oil phases are well known, as well how to incorporate solid agrochemicals insoluble in water to the water phase (e.g., by fine milling). Once the agrochemical to microencapsulated is selected, it needs to be chosen the wall forming materials. As first choice we recommend the use the compounds and proportions referred in the description and examples, as well the indicated ratios. When wanting to incorporate wall forming materials not explicitly disclosed in the examples, then a first assumption on similar reactivity must be made with due care of comments to this respect done before. If the reaction of the isocyanates is not taking place, an increase of the temperature must be done and/or increase of the catalyst, as first choice dibutyltin laurate. If this still does not suffice, then must be considered the reactivity of each isocyanate and exclude the combinations of isocyanates that by virtue of their low reactivity (data available from the manufacturers) are not expected to react. In principle, all ACDs claimed are able to react with combination of aromatic and aliphatic isocyanates, but, again, if this does not happen, then must be increased the reaction temperature and/or the quantity and type of ACD's catalyst (for example change p/ethylsulfonimide by the more strong p-toluensulfonic acid), or modify by error and trial (there is no single theory in this regard in commonly available books) the ratios of the wall forming materials in the provided ranges. The emulsification is a critical step, and in case of phase inversions, must be adapted accordingly the shear stress to the volume and geometry of the vessels. Also, for microcapsules with low content of wall material, care must be taken with too much high shear stress during formation of oil droplets (may break already fast-formed prepolymeric polyurea walls before incorporation of ACDs).

With regard release rates, normal knowledge for the chemist specialized in controlled release formulations is enough in order to select the appropriate isocyanates and ACDs. Obviously, ACDs with longer alkoxy- or hydroxyalkyl- groups will lead to faster release, because bigger pores. Accordingly, the smaller the particle size (obtained also by higher shear stress and use of surfactants in the oil phase) the faster the release rate. Also, the more quantity of wall material in weight % with respect weight of whole filled microcapsule, the slower will be the release.

In the case of microencapsulation of PCMs, it is obvious that a tight wall is desired, following above instructions and using more wall material than for agricultural uses. For this purpose is interesting the use of middle-alkylated chains of ACDs (e.g., N,N'-diethoxymethyl, N'',N'''-dimethylolacetylene carbamide), because although it may increase the pore size on one side with respect to customary state in the art polyurea walls, it increases, on the other side, the flexibility of the microcapsule and resistance against pressure, that is usual in the normal applications of PCMs (specialty fabrics or plastic-foams).

In the case of encapsulation of catalysts, the ACDs provide unique release rates that must be adapted for the purpose of the use of the catalyst: for example, in hydrogenations with microencapsulated polyurea-ACD palladium, under pressure is convenient to reach higher percentages of ACDs in the wall. On the contrary, for applications in biotechnology of osmium tetroxide catalyzed reactions, bigger pores are needed, going to ACDs of relatively high alkyl chains (e.g., tetrabutoxyethyl acetylene carbamide).

With regard specific details about the wall forming materials we disclose, the ACD can be, in some embodiments, characterized in that where the number of substituents $R_2$, $R_4$, $R_6$, $R_8$ is having the meaning of hydrogen in the same particular compound (I) is limited to one or two.

The aromatic isocyanate can be a monomeric aromatic isocyanate or a prepolimer aromatic isocyanate, most preferably a prepolymer aromatic isocyanate.

The aliphatic isocyanate can be a monomer aliphatic isocyanate or a prepolymer aliphatic isocyanate, more preferably a monomer aliphatic isocyanate.

A preferred aromatic isocyanate has the formula (II), and structurally chemical related mono, di and tri isocyanatate substituted toluene oligomerized compounds.

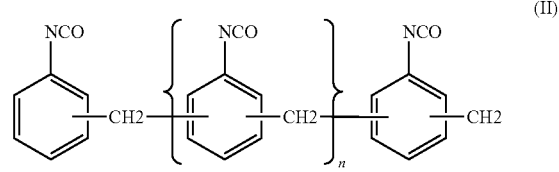

wherein n=0 to n=6, most preferably n=1.

A preferred aromatic isocyanate is diphenylmethane-4-4'-diisocyanate, optionally, and blends of isomers and homologues.

A preferred aliphatic isocyanate is m-tetramethylxylene diisocyanate and/or

The aliphatic isocyanate (even in singular) must be interpreted as optionally a mixture different aliphatic isocyanates, accordingly the same for the aromatic isocyanates.

We direct a claim to a polymer according claim 1 characterized in that the polymer is formed by the reaction of wall forming materials where the ACDs are mixture of different compounds with different substituents according claim formula (I).

Regarding oligomerized ADCs, we explicitly claim mixture of compounds (I) in the form of oligomers up to 10 mols per molecule, being the sum of the quantity of monomers, dimers, trimers and tetramers at least 75% in weight-% of the total ACD mixture as defined in claim 3 in weight-%.

The ACD used may be a single compound represented by the formula (I).

The ACDs can be composed of substituted acetylene carbamide monomeric and/or low oligomerized (from 2 to 10 monomers per molecule) and/or non-polymerized compounds (I), being the content high polymerized monomers—more than 100 monomers per molecule-lower than 10% in weight % with respect the content of monomers in weight percent, preferably less than 0.5% in weight %.

It is also of interest where 100% of the solution of mixed ACDs is composed of monomeric substituted acetylene carbamide derivatives (I) where at least one substituent of $R_1$, $R_2$, $R_3$, $R_4$, $R_5$, $R_6$, $R_7$, $R_8$ is different to the others.

The polymer according any suitable preceding claim or combination of preceding claims characterized in that compound of claim 1 i) (c), is a acetylene carbamide derivative with low hydroxyalkyl content (up to 50%) in such a way the degree of polymerization trough the hydroxyalkyl groups is not too high, allowing a microcapsule's wall formed with the polymer of claim 1 to be conveniently porous for controlled release, being the term suitability of the control release understood as a expert in agrochemistry would interpret at the view of commercially suitable products.

The polymer of claim 1 or 2 characterized in that compound (I), is chosen as a single ACD compound in monomeric and/or dimeric and/or trimeric form, and not as a mixture of different compounds comprised in the formula (I).

A mixture of compound(s) (I) may have a hydroxymethyl content up to 40%, in particular, the sum of number the groups $R_2$, $R_4$, $R_6$, $R_8$ of a compound i) (c) or mixture of compounds i) (c) wherein the groups that take the value of hydrogen is not more than 40% of the total sum of all types of groups $R_2$, $R_4$, $R_6$, $R_8$ in the compound or mixture of compounds.

It can be used any polymer abovementioned characterized in that the solution is mainly—as far as the industrial production of compounds (I) allows it—composed of monomeric compounds (I) where all the substituents $R_1$, $R_2$, $R_3$, $R_4$ are equal among them, $R_5$, $R_6$, $R_7$, $R_8$ are equal among them and $R_9$ and $R_{10}$ are hydrogen atoms.

Preferred ACDs are N,N',N'',N'''-tetrabutoxymethyl acetylene carbamide, N,N',N'',N'''-tetramethoxymethyl acetylene carbamide (Powderlink 1174), N,N',N'',N'''-tetramethoxyethyl acetylene carbamide, N,N',N'',N'''-tetraethoxyethyl acetylene carbamide, N,N',N'',N'''-tetrapropoxymethyl acetylene carbamide.

Most preferred compounds (I) are N,N',N'',N'''-tetramethoxymethyl acetylene carbamide and N,N',N'',N'''-tetrabutoxymethyl acetylene carbamide, to be used alone or in combination.

The compound (I) or mixture of compounds (I) may be used even being solid at 20° C. or more, by means of dissolution or dispersion in the oil phase. In that case, the compound (I) or mixture of compounds (I) is/are dissolved and/or dispersed in a suitable organic solvent to allow the incorporation of the solid into the liquid mixture of polymer forming materials, for example in gamma-butyrolactone or naphtha solvent (Solvesso 100, 150 ND or 200 ND).

We direct a set of claims regarding the process as explained above, but for a more detailed clarification, we will refer to the following:

In brief, we disclose a process of microencapsulation by interfacial polymerization where the continuous phase is water, and the discontinuous phase is water-immiscible phase to be enclosed in microcapsules, this process being performed in a customary interfacial polymerization reaction, characterized in that microcapsule's wall is formed by the reaction of:

aromatic isocyanate
aliphatic isocyanate
substituted acetylene carbamide compound or mixture of compounds of formula (I)

In a more detailed way, we describe a process of production of a microencapsulated formulation comprising one or more substances that remain inside the microcapsules after the production of such formulation, characterized in that:

I) Two phases are prepared:
a) an oil phase is prepared by mixing, dissolving and/or dispersing one or more active materials, and mixing, dissolving and/or dispersing the following components:
a.1.) the polymer-forming materials described in suitable combinations of preceding claims
a.2.) an oil soluble or dispersible catalyst suitable for the formation of a polyurea-substituted acetylene carbamide polymer
a.3.) eventually a solvent or dispersant
a.4.) eventually an oil-soluble surfactant
a.5.) an active ingredient or a mixture of active ingredients, that in the case of agricultural use are active pesticides and related chemicals, in other fields correspondingly the phase change materials, inks, thermosetting materials or what the skilled in the art considers what is the active ingredient—main purpose of the microcapsule—for each particular application
a.6.) eventually additional active ingredients, dissolved or dispersed in the oil phase, coformulants for the stability of the water-immiscible or water-soluble materials, the stability of other coformulants, the stability of the microcapsules, stability of any component against light—by means of organic compounds—, thermal and/or pressure stress and/or microbiological contamination, or the stability of the formulation as a whole.
b) a water phase is prepared by mixing, dissolving and/or dispersing
b.1.) water
b.2.) a single emulsifier or a mixture of emulsifiers
b.3.) a polymer of the type of PVA or PVP or any derivatives thereof, or any mixtures of said polymers
b.4.) a lignosulfonate or a mixture of lignosulfonates
b.4.) optionally a wetting agent
b.6) eventually additional coformulants for adjusting the pH at 6-7 or for improving the stability of the water-immiscible or water-soluble materials, the stability of other coformulants, the stability of the microcapsules, stability of any component against light-specially the active ingredient(s), thermal and/or pressure stress and/or microbiological contamination, or the stability of the formulation as a whole.

II) The oil phase is incorporated to the water phase at about 45-70° C., with agitation, the temperature depending on the reactivity and the catalyst choice in the oil phase, being a final period of high shear stress for a period of some minutes III) This provokes the emulsification of the oil phase into the water phase and at the same time the formation of the microcapsules' wall is beginning to be formed, at a temperature ranging from 60-90° C.

IV) Then it is added a catalyst that provokes the formation a microcapsule's wall of mixed polymer polyurea-substituted acetylene carbamide, V) Stirring of the reaction solution formed, with a very low shearing stress—low enough in order to not to break the microcapsules—for about 1-4 hours VI) Optionally increasing the temperature up to 70-90° C. for step V)

VII) Optionally, addition of coformulants for the purposes of pH final adjustment (from 3 to 12), viscosity modifiers, wetting agents, antifreezing agents, antimicrobials, protectors against light, and any other coformulant suitable for the purposes of the microencapsulated formulation, being possible and optional to add all these compounds or some of them, in the water or oil phases previously described.

We also describe a process unitary with the scope of the invention as a process of producing a formulation of the type capsule suspension, containing an encapsulated water-immiscible material or plurality of water-immiscible materials characterized in that such material is microencapsulated within discrete microcapsules of polyurea-acetylene carbamide copolymer consisting in:

(a) providing, at a temperature from 45° C. to 70° C., preferably from 40° C. to 60°, and most preferably from 40° C. to 55° C., a dispersion of (i) a water-immiscible phase comprising the agricultural active water-immiscible material or materials to be encapsulated, an aromatic isocyanate, an aliphatic isocyanate and an ACD, eventually a suitable solvent for dissolving any preceding compound that may be a solid, eventually a dispersant if the active compound is a solid, and eventually also a surfactant, (ii) an aqueous phase comprising a solution of water, a surfactant or mixtures thereof, a protective colloid or mixtures thereof, a polymer both having surfactant and protective colloid properties; and (b) heating and maintaining said dispersion in a temperature range of 60° C. to 90° C., whereupon said water-immiscible material is encapsulated within discrete polyurea-substituted acetylene carbamide mixed polymer microcapsular enclosures.

(c) once the microcapsules are formed and the encapsulation polymer-forming materials are substantially consumed, optionally adding a water solution containing the coformulants needed for a functionally usable agricultural formulation that include viscosity modifiers, clays or similar mesoporous materials—preferably sepiolite or zeolite—, hydrocolloids, antimicrobiological agents, UV protectants, wetting agents, additional surfactants.

The compound a.4) or b.2) may be a (metha)acrylic graft copolymer and/or is chosen from the group of surfactants: ethoxylated alcohols, ethoxy and/or propoxy block copolymer, poliviniyl alcohol, polyvinyl pyrrolidone and any derivatives or graft copolymers of said surfactants, also chosen from the groups ethoxylated alcohols, ethoxy and/or propoxy block copolymer, polyvinyl alcohol, polyvinyl pyrrolidone and any derivatives or graft copolymers of said surfactants, preferably a polyvinyl fatty acid ester or a polyakyl(metha)crylate with a molecular weight of about 100000 to 200000 Daltons.

The surfactant added to the water phase is a polyethylglycol ester of a polyhydroxy fatty acid with a molecular weight of about 10000 to 25000 Daltons.

One preferred fatty acid in the surfactants is stearic acid.

Regarding our proprietary mixture of lignosulfonates, we claim a process of production of microcapsules according claim 22 characterized in that in the solution I) b) contains a complex consisting in a mixture of, in weight percent, a lignosulfonate at 15-25%, a polyvinyl alcohol at 5-15% and water up to 100%, the compounds chosen in such a way that the lignosulfonates and the polyvinyl alcohol are dissolved in full in water, and this solution is heated up to 60-90° for 5-20 minutes before use in the microencapsulation process.

As a important application of our microcapsules, we claim a process of producing an agricultural formulation of the type suspension concentrate characterized in that:

i) a watery suspension of microcapsules is prepared according claim 31 or 32 steps (a) and (b)

ii) a suspension concentrate in watery media is prepared with the desired active ingredients or a plurality of them (provided that they are chemically compatible in such media and they have a beneficial agricultural use) in a customary way, by means of milling and providing necessary coformulants and optionally, further providing an additional water-soluble active ingredient or a plurality of them (provided that all active ingredients are chemically compatible and they have a beneficial agricultural use), and necessary coformulants iii) mixing the suspensions i) and ii), provided that the mixture of active ingredients have a beneficial agricultural use iv) eventually adding coformulants to the mixture for the formulation stability and functionality, in the case that such coformulants are not already present, or not in the desired amount, in the mixture formed up to this step or optionally they have already being added in the previous steps in the desired amount to be present in the final formulation.

v) eventually filtering the mixture of iii) or iv) to avoid presence of undesirable precipitates that may affect the correct functionality of the suspension concentrate in terms of avoiding blocking of nozzle filters and filters during final application of the suspension concentrate in the field.

Preferred agricultural formulations of microcapsules (in any type of formulation where microcapsules are present) are of the following active ingredients or mixtures thereof (although practically any agrochemical may be microencapsulated, as far as it is soluble, dispersible and stable in the oil phase): fluorochloridone, a pyrethroid and/or a naturally-occurring pyrethrin or mixtures thereof, lambda-cyhalothrin, gamma-cyhalothrin, supercyalothrin, alpha-cypermethrin, clomazone, combinations of fluorocloridone and/or lambda-cyhalothrin and/or clomazone and/or metazachlor and/or alachlor, with other pesticides or agrochemicals, including antidotes, safeners, annelicides and/or semiochemicals, trifluthrin and/or phenothrin, alachlor and/or acetachlor, pendimethalin, trifluralin, organophosphates, chlorpyrifos, endosulfan. fenoxaprop, triazole fungicides, propiconazole, ketoconazole, triadimenol, epoxiconazole, tebuconazole (optionally where the oil phase contains a customary agricultural solvent of the type substituted alkyllactam or N,N-dimethylalkylamide), fluoroxypyr.

By virtue of the removal of toxic isocyanates or at least reduction in quantity and in toxicology profile of them, our microcapsules may be used to microencapsulated pharmaceuticals for its use in medicine.

The best way to understand the complexity invention is trough the examples presented below, that complete the needs of a skilled in the art to reproduce the invention.

Example 1

Here is disclosed the way of preparation of a microencapsulated formulation of Fluorochloridone at a concentration of 25% (wt/wt).

|  | In kg |
|---|---|
| Organic Phase: | |
| Flurochloridone (50%) in Solvesso™ 150 | 500 |
| Benzene, 1,3-Bis(1-isocyanate-1-methylethyl)-diisocyanate (TMXDI) | 10 |
| Diphenylmethane-4,4'-diisocyanate (PMDI) | 18 |
| Dibutyltin laurate | 0.03 |
| Tetraethoxymetyl acetylene carbamide | 4 |
| Gamma-butyrolactone | 3 |
| Water Phase: | |
| Water (added independently from the other solutions) | 232 |
| 10% water solution of xanthan gum | 20 |
| 20% water solution of PVP-30 | 10 |
| 35% water solution of Arabic gum | 50 |
| LignoGAT™ | 40 |
| Antirnussol™ 4459 | 0.25 |
| Citric Acid | 0.14 |
| Reax™ 85A | 0.25 |

LignoGAT™ is a proprietary solution here disclosed composed of water:Celvol™-0 205:Kraftsperse™ 25M in which the ratios vary according (respectively): 60-70%:5-15%:5-30%. In this particular case, the ratio is 65:5:30.

When both phases are well-mixed in a separate reactors [important to note that some heating is needed to incorporate the solid crystals of cis-Fluorochloridone, with a melting point of about 71° C.], they oil phase is incorporated at about 50° C. slowly to the water phase (at 35° C. and pH adjusted to 6.5 with citric acid), emulsifying the organic phase into small droplets in a continuous aqueous phase with a high shear agitator at about 2500 rpm (in a typical cylindrical 2,000 L reactor) for 15 minutes. Then, the high shear agitator is stopped and only an anchor stirrer is set to 50 rpm. The wall forming material present in the organic phase (isocyanates and acetylene carbamide monomer) reacts with water at the oil/water interface to form a pre-wall capsule around the oil droplet containing the active ingredient Fluorochloridone. Temperature is increased to 50° C. at the beginning of reaction. Then 0.15% (w/w) of p-Toluenesulfonic acid (dissolved in isopropanol), is added to terminate polymerization in the water phase side and wall forming reactions. Further, the mixture is at about 48° C. for five hours. This way, it is avoided any residue of isocyanates and/or free acetylene carbamide monomers. Then, the mixture is allowed to cool down. The pH is checked and is adjusted to pH=9.5 to 10 with a 50% watery solution of NaOH. Finally, the following solution for stabilization purposes is added:

|  | In kg |
|---|---|
| NaOH | 3 |
| Water | 64 |
| Keltrol | 0.7 |
| Pangel S9 | 5.5 |
| $Na_2CO_3$ | 4.8 |
| $Al_2(SO_4)_3$ | 0.1 |
| $Na_5P_3O_{10}$ | 0.3 |
| Germal™ II | 0.5 |
| BHA + BHT (ratio 1:1) | 0.5 |
| Cyasorb™ UV-1164L | 1 |

The finished formulation is let to homogenize with an anchor stirrer at 100 rpm, and then is filtered through a 100 μm nylon sieve.

Example 2

Resulting microcapsules according process of Example 1 and comparison with commercial Fluorochloridone CS 250 g/l (Racer™).

The microcapsules of Example 1 are shown in FIG. 1.

The resulting microcapsule according Example 1 have the following parameters:

| SAMPLE | A.I. Tot [wt %] | trans [wt %] | cis [wt %] | ratio trans/cis | density g/cm³ | pH 1% | PS [4.3] |
|---|---|---|---|---|---|---|---|
| Racer CS | 22.25 | 17.26 | 4.99 | 77.56/22.44 | 1.1066 | 10.42 | 14.89 |
| GAT-FLU-1 | 23.34 | 17.31 | 6.02 | 74.18/25.82 | 1.1124 | 9.17 | 13.37 |

|  | Viscosity | | | | Suspensi- | |
|---|---|---|---|---|---|---|
|  | □ at □ˌ [Pa] | Yield Stress [Pa] | □ at □ˌ [Pa] | A.I. Tot g/L | bility % | Unen % |
| Racer CS | 45.32 | ⸺Pa at□□0 | 0.83 | 251 | 75.23 | 0.95 |
| GAT-FLU-1 | 48.12 | ⸺Pa at□□ | 1.26 | 260 | 87.97 | 0.06 |

Note that fluorochloridone has two isomers (cis and trans) with different melting point, and our invention allows encapsulation of both solid and liquid materials (even adsorbed/absorbed/solubilized gas materials in a solid or liquid support) easily.

IR analysis of Racer™ CS show that the capsules' wall is composed of TDI and PAPI, while in our invention the TDI is replaced by the much less toxic and less reactive TMXDI. Our special conditions of encapsulation allow us to match perfectly the physiochemical and chemical (regarding agricultural use) characteristics of Racer™, with a completely different capules' wall composition, protective colloid (by LC-MS identified as type of Daxad™ 23 in Racer™), primary emulsifier (by LC-MS and chemical sample preparation identified in Racer™ as type of Pluronic™ L64), and other coformulants.

Figure 2:
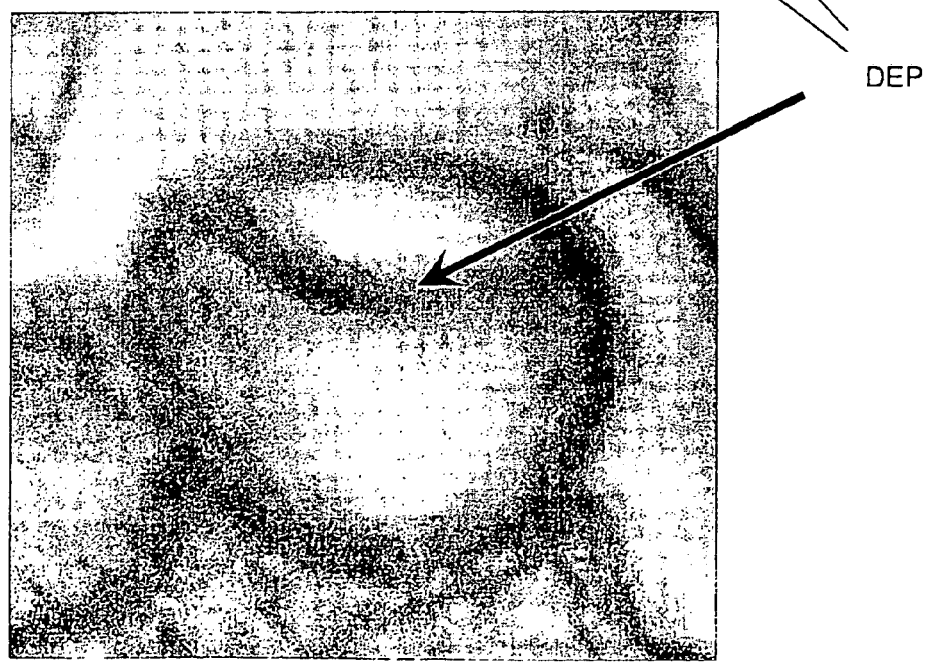

We have observed that the microcapsules according our process show an spherical three-dimensional structure, however, the spheres have sometimes a depression (DEP) in the surface—indicated in FIGS. 1 and 2 by the arrow—(sometimes, the surface corresponding to the invaginated area is almost half of the total capsule's surface), that we have not found in other commercial microencapsulated agrochemicals either in microcapsules for other purposes. The specific reaction TMXDI+PAPI+acetylene carbamide monomer is believed to the reason of this effect.

The determination of unencapsulated active ingredient is made as follows (for this and the rest of the examples):

Filtration of the formulation sample suspended in water:
  100 mg of CS sample suspended in 15 ml water-dipropylene glycol mix Filter through glass fiber filter
Wash with 2×5 ml water-dipropylene glycol mix
Determination of a.i. in the filtrate by HPLC-UV or GC-FID analysis
The HPLC conditions we used normally were L iChrospher 100 CN—5 pm, 250×4 mm; Column thermostat: 32° C.; Injection volume: 10 μl; Mobile phase: 97% (v/v) n-Hexane, 3% (v/v) Isopropanol; Flow: 1 ml/min; Detector: at 240 nm; Analysis time: 35.0 minutes.

Example 3

Figure 3:
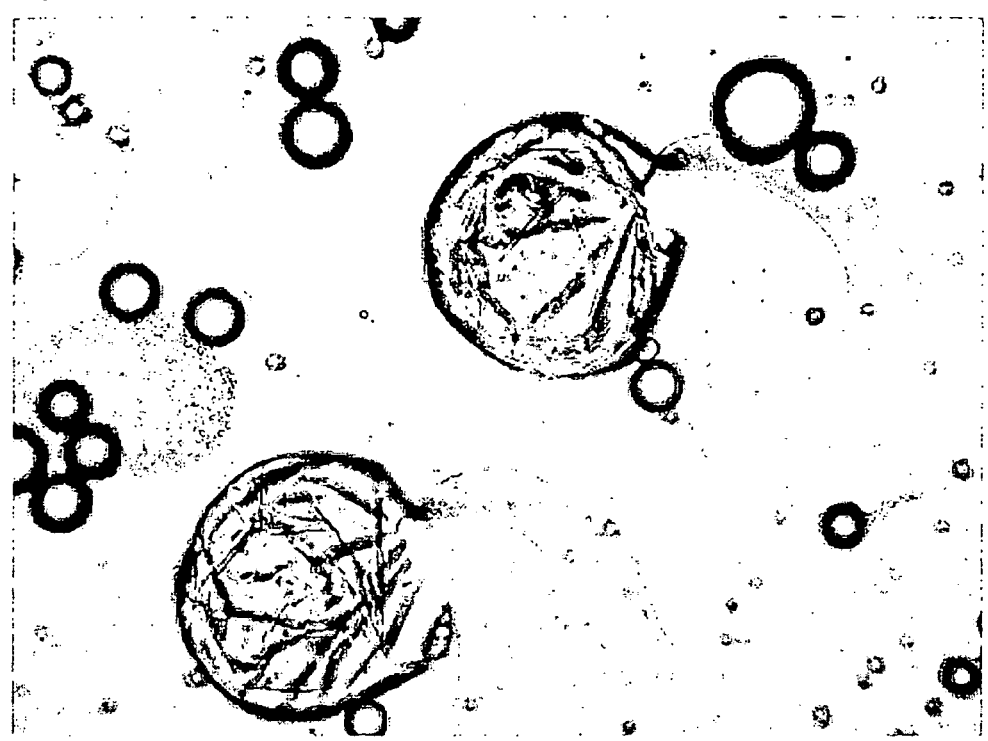
FIG. 3 shows a microcapsules releasing material.

A formulation as described in Example 1 was made, in which the wall forming material was replaced by the prepolymerized etherified urea formaldehyde resin, Beetle™ 80, being the prepolymerization based on the process suggested in U.S. Pat. No. 6,485,736. Then the whole quantity of Tetramethoxymethyl acetylene carbamide and isocyanates were substituted accordingly from the wall forming materials, and the gamma-butyrolactone removed from the formula. A detail of the microcapsules present in the formulation of fluorochloridone just after finishing the process exactly carried out as in example 1 (with the above modifications) (detail in FIG. 3), being the particle size irregular, and that the microcapsules are bigger and release immediately the content into the water phase. The mean particle size is 29.3 μm, and the percentile 90 is 71.64 μm, making the microcapsules inadequately big and too fragile.

Example 4

In the laboratory, further formulations as in Example 3 were prepared, using the same wt % ratios as in example 1, but for 1 L of finished formulation. 14 reactors with cooling and heating system (water shirt) of volume 2 L were set in series.

Figure 4:
FIG. 4 shows the crystals that appear after a failed or defective microencapsulation; microcapsules releasing oil from the inside of the microcapsule are also shown that corresponds to Example 4-1 after 240 hours at 35° C.

After final emulsification, corresponding pH adjustments and final stability solution addition, stirring and allowing the final mixture to reach room temperature, the particle size was immediately measured, meaning Perc. 90 the statistic "Percentil 90" (10% of the microcapsules have a mean diameter than the value given). The active ingredient unencapsulated is measured by centrifugation the microcapsules and then analyzing the supranatant in a GC-FID, with a validated analytical method. The emulsion stability was tested according the FAO/WHO specifications for emulsion stability of lambda-cyhalothrin CS (a formulation of the same type (capsules suspension), this document incorporated herein by reference. Only values with "very good emulsion stability" score comply with the requirements of oil/cream separation and formation of crystals in the emulsified formulation in water. The crystallization has been subjectively (but consistant in between appreciations of different samples) ranked, according to observation of 5 samples of the undiluted formulation at the microscope at objectives ×10 and ×40. In FIG. 4 we show the crystals in Ex. 4-1 after 240 hours of storage at 35° C.

Results are as follows:

|  |  | particle size in μm | | a.i. | Observations -storage for | |
| --- | --- | --- | --- | --- | --- | --- |
|  |  | average | Perc. 90 | unencapsulated | cryst. At 35° C.- | |
| Ex. 4-1 | Cymel ™ 350 | 28.3 | 98.0 | 30% | very high crystallization after 240 h | + bad emuls. stability |
| Ex. 4-2 | Dynomin ™ MM9IIp | 54.5 | 133.7 | 49% | very high crystallization after 240 h | + bad emuls. stability |
| Ex. 4-3 | Cymel ™ 323 | 26.0 | 84.6 | 15% | medium crystallization after 240 h | + good emuls. stability |
| Ex. 4-4 | Cymel ™ 1168 | phase inversion - no formation of microcapsules | | | | – |
| Ex. 4-5 | Cymel ™ 1116 | 32.2 | 54.9 | 18% | medium crystallization after 240 h | + bad emuls. stability |
| Ex. 4-6 | Dynomin ™ MB-14-B | 67.4 | 154.8 | 5% | low crystallization after 240 h | + bad emuls. stability |
| Ex. 4-7 | Cymel ™ 1156 | 19.6 | 79.9 | 19% | medium crystallization after 240 h | + good emuls. stability |
| Ex. 4-8 | Cymel ™ 1125 | 11.8 | 38.7 | 13% | very low crystallization after 240 h | + good emuls. stability; very fragile microcapsules |
| Ex. 4-9 | UFR ™ 60 | 21.0 | 174.4 | 11% | medium crystallization after 240 h | + very bad emuls. stability |
| Ex. 4-10 | UI-27-IX ™ | 11.9 | 178.2 | 29% | very high crystallization after 240 h | + very bad emuls. stability |
| Ex. 4-11 | Cymel ™ 1172 | 14.8 | 21.9 | 2% | very low crystallization after 240 h | + very good emuls. stability |
| Ex. 4-12 | Cymel ™ 1171 | 17.6 | 29.9 | 3% | very low crystallization after 240 h | + very good emuls. stability |
| Ex. 4-13 | Cymel ™ 1170 | 9.1 | 21.3 | 1% | very low crystallization after 240 h | + very good emuls. stability |

-continued

|  |  | particle size in μm | | a.i. | Observations -storage for cryst. At 35° C.- | |
|---|---|---|---|---|---|---|
|  |  | average | Perc. 90 | unencapsulated | | |
| Ex. 1 | Powderlink ™ 1174 | 7.8 | 16.7 | 0% | no crystallization after 240 h | + very good emuls. stability |

Figure 5:
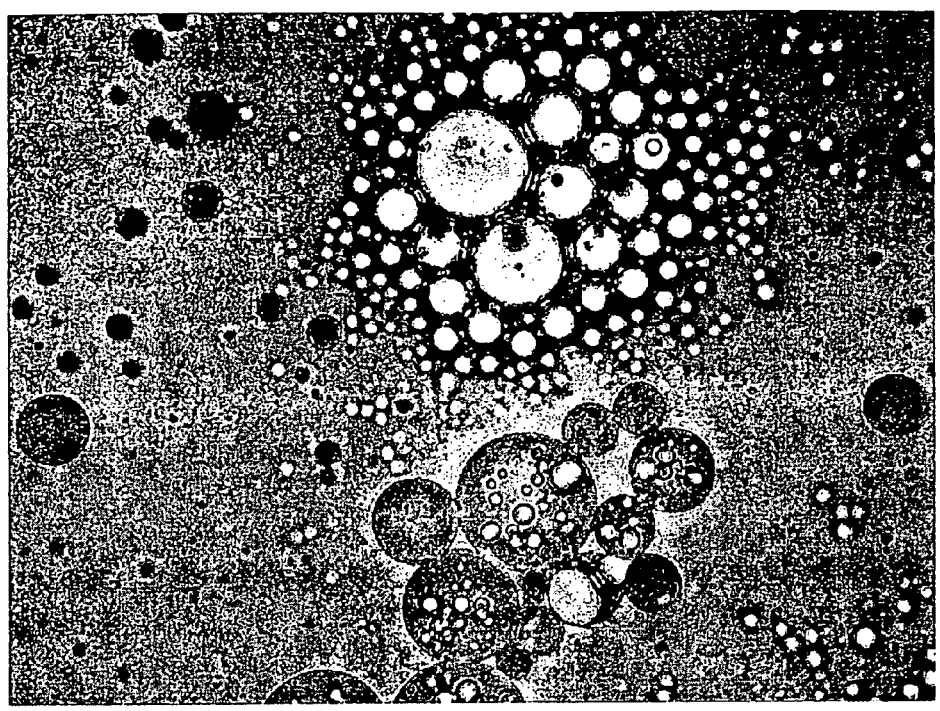
FIG. 5 shows agglomeration of microcapsules.

We can observe that the only acceptable formulations are those formulated with ACDs, and of these, those commercial compounds containing a significant amount of monomers (or dimers or timers) (Ex 4-11, 4-12, 4-13 and 1) give the best results. However those acetylene carbamide cross-linkers containing a lower amount of monomers result in higher particle sizes. Ex. 4-8, based on a benzoguanamin resin, is interesting in the sense of that the particle size of the microcapsules is very appropriate, presents a very good emulsification properties, but we realize that only with manipulation for observing the capsules in the microscope a significant part of them are broken. All the melamine and urea compounds showed a bad performance, with high amounts of unencapsulated Fluorochloridone and subsequent formation of crystals. In examples 4-8, we could observe reversible agglomeration as shown in FIG. 5.

Example 4

In the following example, we have used a different primary emulsifier and protective colloid system. As in previous examples, we refer to Example 1 as a model, and here we perform some modifications The solution LignoGAT™, based in a polymeric product of reaction containing lignosulfonates has been replaced (and in the same quantity) by Agrimer™ AL10 and PVP 15 (ration in wt. % 1:1). In this process we have microencapsulated Quizalofop-pethyl dissolved in Solvesso 100 at 50% (warm).

In order to reduce the particle size (that is expected to be bigger because the change of LignoGAT™ to this new mixture) the speed of the high shear stress stirrer has been increased to 3500 rpm for 5 minutes. The resulting microcapsules had a mean particle size of 5.1 μm and a percentile 90 of 8.3 μm. Emulsification properties (5% of the formulation in water in a 100 mL measuring cylinder) show no separation of phases after 2 h, no crystal formation. The wet sieving residue −150 μm—, was 0.03% and dispersibility and suspensibility were, respectively, 81% and 89%.

Example 5

In this example we microencapsulate according Example 1 with same components and proportions (to make 1 L of formulation) except the following:

Ex. 5-1: isocyanate mixture TMXDI and PAPI and Powderlink™ 1174 [exactly like in Ex. 1]

Ex. 5-1: isocyanate mixture TDI and PAPI.

In both trials we have encapsulated fenvalerate, also dissolved in an hydrocarbon-based solvent at 50% (Marco™)— with previous mild warming to 50° C. and mixing, then letting the mixture to cool down. The final formulation is then an Esfenvalerate 250 g/l Capsules Suspension (assuming density=1 g/cm³).

Results are shown in the following table:

| Process as in Ex. 1 | | | | |
|---|---|---|---|---|
| | | particle size in μm | | a.i. |
| | | average | Perc. 90 | unencapsulated |
| Ex. 5-1 | TMXDI + PAPI | 0.9 | 1.5 | 0.9% |
| Ex. 5-2 | TDI + PAPI | 3.8 | 23.2 | 31% |

As we can see, the reaction with TDA and PAPI resulted in a acceptable particle size of the capsules formed, however the amount of unencapsulated material was too high (32%)—analysis by centrifugation and HPLC-UV of supranatant—. We observed that the reaction proceeded with vigorous develop of $CO_2$, and a sudden temperature increase was noticed (the 2 L reactor went up to 75° C. in Ex. 5-2, while the Ex. 5-1 the maximum temperature registered was 58° C.). Observation under the microscope showed that a number of microscopic pieces of wall material had reacted without forming a wall (thus no microencapsulated material). All these pointed out that the process with the more reactive TDI was uncontrolled (not enough time to allow a good emulsification at the same time that the wall material is formed), namely, the process with TDI is less predictable and less able to be manipulated than the process with TMXDI+PAPI+ACD.

Example 6

A formulation of lambda-cyhalothrin was made according to the following formula (500 L). We have splitted the components according their functionality. The first Table Ex. 6.1 is referring for the water phase and the oil phase up to the emulsification/encapsulation needed materials. In Table Ex. 6.2 we have the compounds that account for the stability of the formulation. To achieve 100% of the formulation,

TABLE EX. 6.1

| Components of the Basic Microencapsulation Materials (BMM) | |
|---|---|
| BMM | Wt.-% |
| OIL PHASE | |
| lambda cyhalothrin | 20 |
| Solvesso 150 | 30 |
| 0-Butyrolactone | 0.22 |
| Powderlink 1174 | 3 |
| TMXDI | 5 |
| PAPI | 1 |
| acrylic graft copolymer | 0.6 |
| dibutyltinlaurate | 0.005 |
| WATER PHASE | |
| Water | 29.1 |
| 5% Agrimer-AL-10 in water | 4.5 |

TABLE EX. 6.1-continued

Components of the Basic Microencapsulation Materials (BMM)

| BMM | Wt.-% |
|---|---|
| 20% carboxymethylcellulose in water | 4 |
| 30% gamma-cyclodextrin in water | 1 |
| LignoGAT | 2 |
| Antimussol 4459 | 0.1 |
| Citric. Ac | 0.02 |
| polyvinyloleate polyethylenglycol ester (80,000 D) | ester 8 |
| Cycat 4040 | 0.15 |
| TOTAL | 100 |

TABLE EX. 6.2

STABILITY MIXTURE + BMM

| | wt (%) |
|---|---|
| Water | 33.3 |
| Propylenglycol | 6 |
| Germal II | 0.05 |
| Atlox 4913 | 0.8 |
| 5% Agrimer AL-10 in water | 1.5 |
| 25% *Ceratonia siliqua* gum in water | 1.5 |
| GAT-3818 | 1.8 |
| 5% Hostaphat B310 | 0.7 |
| 20% PVA in water | 10 |
| Proxel ® | 0.1 |
| BMM | 44.25 |
| TOTAL | 100 |

Encapsulation conditions of the abovementioned components were:

Emulsification done very slowly (according to total volume) to avoid phase inversion while anchor stirrer at 100 rpm and cowless stirrer at 1500 rpm.

Temp. of reaction: 50° C.

High shear stress agitator at 6000 rpm for 5 minutes during encapsulation (MDH). Addition of Cycat 4040.

Curing of microcapsules at 55° C. for 4 hours.

The characteristics of this formulation are the following (all measured parameters standardized by FAO specifications and/or CIPAC methods):

| | |
|---|---|
| Lambda Cyhalothrin: | 10.05 g/L |
| Suspensibility (CIPAC MT.161): | 99 wt-% |
| pH range (CIPAC MT.75.2): | 6.4 +/− 0.5 |
| Particle size by Laser Mastersizer Micro 2.18: | $D[v, 0.5] = 1.05$ μm<br>$D[v, 0.9] = 2.28$ μm |
| Viscosity by Haake Rheowin Pro 2.67: | η(viscosity) in Pas at $\tau_1$ (1.0) = 2.73<br>η(viscosity) in Pas at $\tau_{10}$(10.0) = 0.08<br>yield point($\tau_0$) in Pa at γ = 0 = 7.41 |
| Density at 20° C. (A. Paar DMA 38): | 1.0318 +/− 0.0012 g/mL |

Example 7

Our microencapsulation process differs with respect with all published patents being used in an industrial scale worldwide for agrochemicals in the basic chemistry involved, the nature and structure of the wall and the physicochemical characteristics of the microcapsule itself. However, to be able to make use of our invention, is a further objective to be able to accomplish the release rate, and the chemical equivalence of the inert ingredients to already registered products already in the market (for marketing permits purposes). Underlying our own invention, and surprisingly, we have found that with the correct choice of appropriate acetylene carbamide compounds, surfactant and stabilization system and reaction conditions, the physicochemical characteristics of the commercial formulations as a whole (namely, the parameters regarding laws like EEC 91/414, FAO/WHO Specifications, etc) may be accomplished by our invention, surpressively and in rather different way to the previous art. It is precisely the choice of low reactive glycolurils, the mild conditions of reaction (temperatures much lower than teached in prior art documents), the avoidance of further amines or sulfurated compounds as catalysts or wall forming materials, and the termination accomplished by organic acids, what allow us to make tailor-made formulations with a targeted release rate (whether fast oder prolonged) and biological efficacy.

In order to demonstrate this, we have made a comparison of our microencapsulated process for obtaining a commercial formulation of lambda-cyhalothrin according EEC 91/414. The reference material is a sample of Karate™ Zeon 10 CS.

Encapsulation of GAT Lambda-cyhalothrin 10 CS (GAT-ICy) was done according to the process described in Ex 6 (with regard of an extensive explanation of the process, this has being disclosed in full in previous examples and/or in the description). The above given values are always a mean of 10 different samples, and statistical differences are evaluated by t-student's test, with appropriate transformation for normalization of data by arcsin(sqrt(x)) for percentage values.

In FIG. 7 we can see that the particle size of the formulation is very similarly distributed according to our invention, but differences are not significant, either in mean or percentile 90, and both products comply with FAO Specifications.

Regarding suspensibility, FAO specifies a minimum of 80% Lambda-Cyhalothrin found in suspension after 30 minutes in CIPAC standard water D. Both products are well above of the minimum, GAT-ICy and KZ showed equally 99.2% of suspensibility, with no significant differences in t-Student's test.

The spontaneity of dispersion in [%] was determined according to CIPAC MT 160. The FAO specifies a minimum of 90% Lambda-Cyhalothrin found in suspension after 5 minutes in CIPAC standard water D at 30±2° C. GAT-ICy shows 92% of dispersion, while KZ shows 94%, but with no significant differences in the t-Student's test.

The pourability in [%] was determined according to CIPAC MT 148. Regularly, the viscosity is measured in the laboratory to predict how the pourability will be (it is faster, cheaper and easier to measure the viscosity), but the FAO specifications only point out to this test of pourability, because is the "real" effect on how the viscosity can influence the product: namely, make it difficult to handle or, in particular, to take the content out of the agrochemical package or bottle, and to rinse the bottles for environmental reasons. The FAO specifies a maximum "residue" of 1.5%. The pourability of GAT-ICy is equivalent to the pourability of KZ and complies with the FAO Specification 463/CS (2003) for the "residue after rinsing". Values (having no significant statistical differences) were:

Residue and residue after rinsing, respectively, for GAT-ICy: 2.6% and 0.3%

Idem for KZ: 2.1% and 0.3%, with not statistical significant differences.

The persistent foam in [mL] after 1 minute was determined according to CIPAC MT 47.2. and none of the 30 samples presented any persistent foam after 1 minute.

All together, both samples comply with FAO specifications and they not differ statistically in any value.

Example 8

Release Rate of GAT-ICy and KZ.

For the release rate we have used the OECD guideline for the testing of chemicals No. 428. The formulations tested have been (pairwise) GAT-ICy 10 g/L and GAT-ICy 5 g/L (produced according example 6) compared with Syngenta products of same characteristics (KZ 10 g/L and KZ 5 g/L). One experimental trial was performed for each sample.

The results are shown in FIGS. 8 and 9. It can be appreciated that GAT-ICy has initially a faster release in both types of samples (due to the partially broader pores in the microcapsules originated by the four-fingered acetylene carbamide used). However, at the conditions of the analysis, the content of lambda cyhalothrin in the receptor cells in the case of KZ (both 5 CS and 10 CS) is lower.

Example 9

A suspoemulsion was made containing 250 g/L of Metazachlor and 33.3 g/L of Clomazone. In a suspoemulsion, a solid finely milled or dispersed or emulsified active ingredient is in the continuous water phase, while the discontinuous phase is constituted by microcapsules. We refer in this example how to prepare the microencapsulated part of the suspoemulsion, namely, microcapsules of clomazone. The suspension concentrate that forms part of the formulation, being that concentrate a milled and dispersed Metazachlor (technical was produced according the expired patent DE 2849442, more exactly according the example that discloses monoclinic metazachlor suspension. Metazachlor can also be produced according to EP 12216 according examples 2 (a) or (b) or example 4 (a) or (b) or (c).

The formula of the capsule suspension of clomazone consists in the following ingredients, being the process as the one used for microencapsulation of lambda-cyhalothrin:

| Ingredients | parts |
|---|---|
| Oil phase | |
| Powder link 1174 (60% in gamma - butyrolactone) | 0.80 |
| Specflex NE 138 Isocyanate (PAPI) | 2.25 |
| TMXDI | 1.12 |
| Clomazone technical | 45.00 |
| Catalyst I (dibutyltindilaurate) (1% in solvesso 200) | 0.14 |
| Soft complex | 1 |
| Water | 89.80 |
| Agrimer AL10LC | 3.00 |
| Agrimer VEMA | 1.00 |
| Reax 100 | 5.00 |
| Kraftsperse 25 M | 1.00 |
| Ascorbic acid | 0.20 |
| Water phase | |
| Soft complex | 50.65 |
| Antifoam | 0.015 |
| Germal II | 0.025 |
| Catalyst II | |
| Cycat 4040 | 0.15 |

The suspension concentrate of Metazachlor alone is prepared following the recipe:

| Metazachlor formulation | JF01 030805 wt-% |
|---|---|
| General Water Phase | |
| Water | 57.64 |
| Atlas G-5000 | 14.70 |
| Atlox 4913 | 13.40 |
| Antimussol 4459 | 0.034 |
| PVP K90 Solution (5% in water) | 13.30 |
| Phosphoric acid 85% | 0.02 |
| Sodium hydroxide | 0.51 |
| Germall ® II | 0.07 |
| Metazachlor SC concentrate | |
| General water phase | 48.90 |
| Metazachlor technical | 51.10 |

Then the suspended Metazachlor is mixed with the capsule suspension of clomazone in the following way:

| Ingredients | Parts |
|---|---|
| Metazachlor concentrate (as above) | 51.8942 |
| Clomazone concentrate (as in abovementioned table) | 6.7418 |
| Water | 24.8534 |
| PVP K90 Solution (5%) | 3.0000 |
| Madeol | 2.5000 |
| Atlox 4913 | 5.0000 |
| Keltrol (2% in water) | 1.5106 |
| Pangel (1% in water) | 5.0000 |

Figure 6:
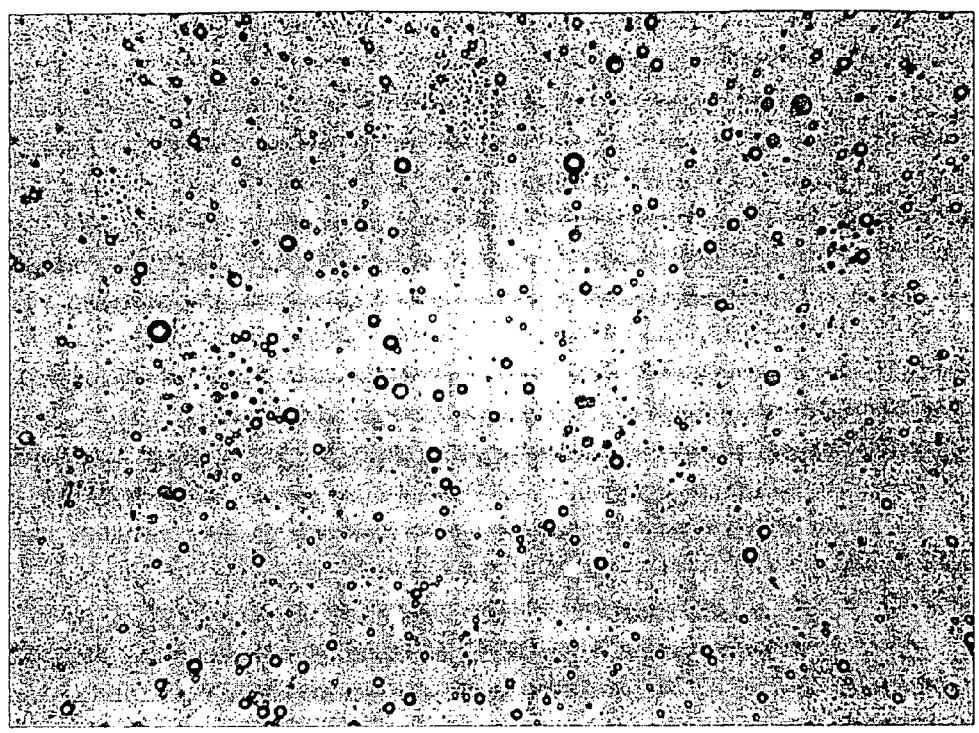
FIG. 6 shows a well-dispersed formulation of microcapsules, from Example 9.

This formulation has the characteristics shown in FIG. 11 (particle size) and FIG. 12 (viscosity). A picture of the microcapsules is shown in FIG. 6.

Example 10

A flame retardant material (antimony oxide) was microencapsulated according this invention together the phase change material (PCM) perfluorodecane, according the process disclosed in this invention. The water phase was later sprayed dried in order to obtain a fluid formulation of microcapsules.

Example 11

The following microencapsulations of fluoroxypyr were done, according the formula of clomazone capsule suspension example 9, and the water phase of example 6. As a comparative test we performed the microencapsulation according the state of the art using TDI and PAPI, that showed an average particle size of 2.73 μm and a percentile 90 of 15.79 μm.

Figure 10:
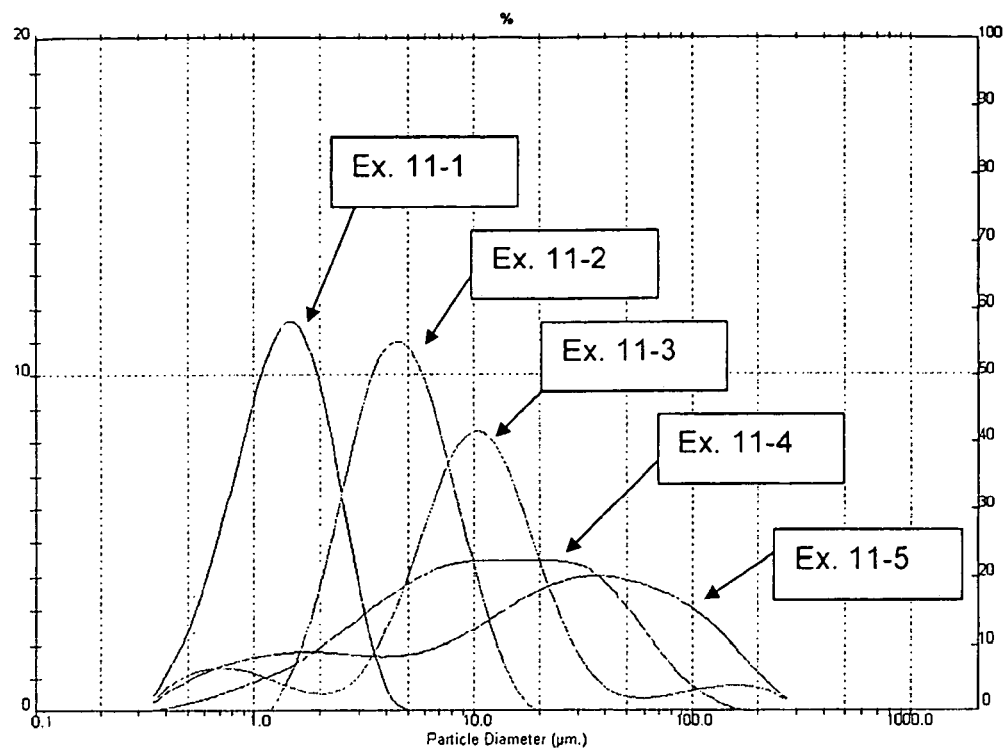
FIG. 10 shows different particle size distributions according Example 11.

The measurements of each example are represented in FIG. 10, and were done accordingly to the microcapsules themselves.

We tested the wall forming material when composed of:

| Specflex NE 138 | 2.25 parts |
|---|---|
| TMXDI | 1.12 parts |

ACD as follows:

| | |
|---|---|
| Example 11-1 Trimetoxymethoxymethyl monometylol acetylene carbamide | 0.80 parts |
| Example 11-2 Tetramethoxymethyl acetylene carbamide | 0.80 parts |
| Example 11-3 Tetramethoxymethyl acetylene carbamide | 0.90 parts |
| Example 11-4 Tetrabutoxymethyl acetylene carbamide | 0.50 parts |
| Example 11-5 Tetrapenthoxybutoxyl acetylene carbamide | 1.00 parts |

The results are shown in FIG. 12, where differences are appreciated according the type and quantity of acetylene carbamide derivative.

Example 12

Two formulations were made: the one according example 6 (Ex. 12-1) and the same formulation but replacing the wall forming material TMXDI by TXDI, and removing the presence of 3% of tetramethoxymethyl acetylene carbamide (ex. 12-2).

The content of residual isocyanates was tested by derivatization of the sample with 1-(9-anthracenenylmethyl) pyperazine and detection at 254 nm on the HPLC-UV. Since the purpose of the analysis was comparative, it was not made a quantitation in weight percent. However, the AU units of the UV-absorption is a definite check (for equally injected 10 μL from solutions 50 mg/mL in acetonitrile of sample) to compare the amount of residual TDI, TMXDI and PAPI (as far as they coelute simultaneously). The results showed that Ex. 12-1 had AU value of 641 mV (above limit of detection), while Ex. 12-2 had AU value of 11 mV (below limit of detection). Thus, the use of ACD prevented the presence of residual isocyanates in the agrochemical formulation.

The invention claimed is:

1. A composition comprising microcapsules that each enclose one or more microencapsulated materials having a solubility in water lower than 750 mg/L at 20° C.,
wherein a wall of each of the microcapsules is formed by means of an interfacial polymerization reaction of wall forming materials comprising:
one or more aliphatic isocyanates,
one or more aromatic isocyanates, and
one or more compounds of formula (I)

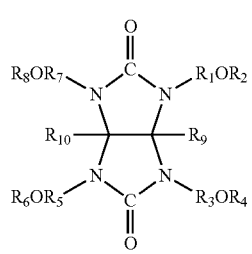

where $R_1$, $R_3$, $R_5$, $R_7$ are, independently one to each other, methylen, ethylen, n-propylen, isopropylen, n-butylen, isobutylen, sec-butylen, tert-butylen, $R_2$, $R_4$, $R_6$, $R_8$ are, independently one to each other, hydrogen, methyl, ethyl, n-propyl, isopropyl, n-butyl, isobutyl, sec-butyl, tert-butyl, and $R_9$, $R_{10}$ are each hydrogen or hydroxymethyl; and
wherein the microcapsules have a mean diameter of 0.3 to 25 μm, when measured with a conventional laser diffraction particle sizer analyzer, previous customary dilution upon water under agitation; and wherein 90% of the microcapsules have a diameter lower than 100 μm.

2. The composition according to claim 1, wherein the ratio of aliphatic:aromatic isocyanates is from 1:3 to 1:1; wherein the ratio of aromatic isocyanates to compounds (I) is from 9:1 to 4:1; wherein the ratio of aliphatic:compounds (I) is from 2:1 to 5:1, and wherein the ratio of aliphatic:aromatic isocyanates:compounds (I) is 3:6:1.

3. The composition according to claim 1, wherein the one or more aromatic isocyanates are one isocyanate having the formula (II):

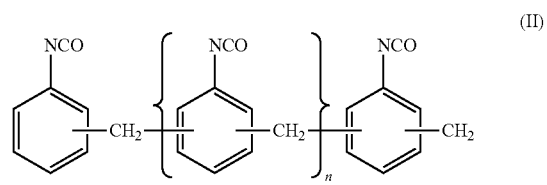

wherein n=0 to n=6.

4. The composition according to claim 1, wherein the one or more aromatic isocyanates are one aromatic isocyanate.

5. The composition according to claim 1, characterized in that the compound (I) is N,N',N'',N'''-tetrabutoxymethyl acetylene carbamide or N,N',N'',N'''-tetramethoxymethyl acetylene carbamide or N,N',N'',N'''-tetramethoxyethyl acetylene carbamide or N,N',N'',N'''-tetraethoxyethyl acetylene carbamide or N,N',N'',N'''-tetrapropoxymethyl acetylene carbamide.

6. The composition according to claim 1, wherein at least one microencapsulated material of the one or more microencapsulated materials is selected from the group consisting of: flurochloridone, pyrethroids, naturally-occurring pyrethrins or mixtures thereof, lambda-cyhalothrin, gamma-cyhalothrin, supercyhalothrin, deltamethrin, alpha-cypermethrin, clomazone, trifluthrin, phenothrin, alachlor, acetachlor, pendimethalin, trifluralin, organophosphates, chlorpyrifos, endosulfan, fenoxaprop, triazole fungicides, tebuconazole, propiconazole, ketoconazole, triadimenol, epoxiconazole and fluroxypyr.

7. The composition according to claim 1, wherein the composition comprises an agrochemical formulation, wherein the one or more microencapsulated materials enclosed in each of the microcapsules comprise combinations of fluorochloridone and/or lambda-cyhalothrin and/or clomazone and/or metazachlor and/or alachlor, with other pesticides or agrochemicals, including antidotes, safeners, annelicides and/or semiochemicals.

8. The composition according to claim 1, wherein the one or more microencapsulated materials comprise tebuconazole.

9. The composition according to claim 1, wherein the composition comprises an agrochemical formulation characterized in that the microencapsulated material is part of an agrochemical capsule suspension, or a capsule suspension and suspension concentrate, or water dispersable granules.

10. The composition according to claim 1, wherein the herbicide clomazone is microencapsulated in the microcapsules to form a capsule suspension and this capsule suspension is formulated together with a suspension concentrate of metazachlor to give a formulation of metazachlor and clomazone.

11. The composition according to claim 1, wherein the microcapsules are present in any formulation type suitable for agricultural use.

12. The composition according to claim 1, wherein the microcapsules encapsulate a member of the group consisting of: pharmaceutical compounds, medicinal compounds, flame retardants, phase change materials, thermosetting materials, inks, and catalysts.

13. A method comprising the following steps:
(a) heating an emulsion comprising an oil phase emulsified in a water phase to a temperature of about 60 to 90° C. to thereby form pre-wall capsules around oil droplets of an oil phase of the emulsion,
the oil phase comprising the following components:
  (1A) one or more aliphatic isocyonates,
  (1B) one or more aromatic isocyanates,
  (1C) one or more acetylene carbamide derivatives,
  (1D) one or more active ingredients having a solubility in water lower than 750 mg/L at 20° C. that is contained in oil droplets,
  (1E) a first catalyst that catalyzes a polymerization reaction between the one or more aliphatic isocyonates and the one or more aromatic isocyanates at an oil/water interface between the oil phase and the water phase to thereby form the pre-wall capsules
  (1F) a solvent or dispersant, and
  (1G) an oil-soluble surfactant; and
the water phase comprising the following components:
  (2A) water,
  (2B) one or more emulsifiers,
  (2C) a polymer comprising polyvinylpyrrolidone (PVP) and/or polyvinyl acetate (PVA), and/or copolymers of PVP and/or PVA, and/or derivatives of PVP and/or PVA, and
  (2D) one or more lignosulfates; and
(b) adding a second catalyst to the water phase of the emulsion that catalyzes a reaction that incorporates the one or more acetylene carbamide derivatives into the pre-wall capsules to thereby form microcapsules enclosing the one or more active ingredients;
wherein each of the acetylene carbamide derivatives is a compound of formula (I)

$$\text{(I)}$$

where $R_1$, $R_3$, $R_5$, $R_7$ are, independently one to each other, methylen, ethylen, n-propylen, isopropylen, n-butylen, isobutylen, sec-butylen, tert-butylen $R_2$, $R_4$, $R_6$, $R_8$ are, independently one to each other, hydrogen, methyl, ethyl, n-propyl, isopropyl, n-butyl, isobutyl, sec-butyl, tert-butyl, and $R_9$, $R_{10}$ are each hydrogen or hydroxymethyl; and
wherein the microcapsules have a mean diameter of 0.3 to 25 µm, when measured with a conventional laser diffraction particle sizer analyzer, previous customary dilution upon water under agitation; and wherein 90% of the microcapsules have a diameter lower than 100 µm.

14. The method of claim 13, wherein the active ingredient is selected from the group consisting of: flurochloridone, pyrethroids, naturally-occurring pyrethrins or mixtures thereof, lambda-cyhalothrin, gamma-cyhalothrin, supercyhalothrin, alpha-cypermethrin, clomazone, trifluthrin, phenothrin, alachlor, acetachlor, pendimethalin, trifluralin, organophosphates, chlorpyrifos, endosulfan, fenoxaprop, triazole fungicides, tebuconazole, propiconazole, ketoconazole, triadimenol, epoxiconazole and fluroxypyr.

15. The method of claim 13, wherein components (1A), (1B) and (1C) are wall forming materials, wherein the oil phase comprises a block copolymer with a hydrophilic to lipophilic balance of about 3 to 7 and wherein the block copolymer is present in the oil phase at a concentration of 5 to 25% with respect to a total amount of the wall forming materials.

16. The method of claim 13, wherein the oil phase comprises one or more members of the group consisting of: coformulants for stabilizing water immiscible or water-soluble materials of the emulsion, coformulants for stabilizing other coformulants of the emulsion, coformulants for stabilizing the microcapsules, coformulants for stabilizing components of the emulsion against light, coformulants for stabilizing components of the emulsion against thermal stress, coformulants for stabilizing components of the emulsion against pressure stress, coformulants for stabilizing components of the emulsion against microbiological contamination, coformulants for stabilizing the emulsion.

17. The method of claim 13, wherein the water phase comprises one or more members of the group consisting of: coformulants for adjusting the pH of the water phases to 6-7, coformulants for stabilizing water immiscible or water-soluble materials of the emulsion, coformulants for stabilizing other coformulants of the emulsion, coformulants for stabilizing the microcapsules, coformulants for stabilizing components of the emulsion against light, coformulants for stabilizing components of the emulsion against thermal stress, coformulants for stabilizing components of the emulsion against pressure stress, coformulants for stabilizing components of the emulsion against microbiological contamination, coformulants for stabilizing the emulsion.

18. The method of claim 13, wherein the oil-soluble surfactant and/or the one or more emulsifiers are selected from the members of the group of surfactants consisting of: ethoxylated alcohols, ethoxy and/or propoxy block copolymers, polyvinyl alcohols, polyvinyl pyrrolidones and any derivatives or graft copolymers thereof.

19. The method of claim 13, wherein the one or more emulsifiers are selected from the members of the group consisting of: polyethylglycol ester of a polyhydroxy fatty acid with a molecular weight of about 10,000 to 25,000 Daltons.

20. The method of claim 13, wherein the oil-soluble surfactant and/or the one or more emulsifiers are selected from the members of the group consisting of: polyvinyl fatty acid esters and a polyakyl(metha)acrylates with a molecular weight of about 100,000 to 200,000 Daltons.

21. The composition according to claim 1, wherein said aromatic isocyanate is diphenylmethane-4-4'-diisocyanate.

* * * * *